(12) United States Patent
Tateyama et al.

(10) Patent No.: US 10,309,877 B2
(45) Date of Patent: *Jun. 4, 2019

(54) METHOD FOR ANALYZING ATYPICAL CELLS IN URINE, URINE ANALYZER, AND METHOD FOR ANALYZING ATYPICAL CELLS IN BODY FLUID

(71) Applicant: Sysmex Corporation, Kobe-shi, Hyogo (JP)

(72) Inventors: Shota Tateyama, Kobe (JP); Masanori Kawano, Kobe (JP); Masatsugu Ozasa, Kobe (JP)

(73) Assignee: Sysmex Corporation, Kobe (JP)

( * ) Notice: Subject to any disclaimer, the term of this patent is extended or adjusted under 35 U.S.C. 154(b) by 219 days.

This patent is subject to a terminal disclaimer.

(21) Appl. No.: 14/831,244

(22) Filed: Aug. 20, 2015

(65) Prior Publication Data
US 2016/0054222 A1 Feb. 25, 2016

(30) Foreign Application Priority Data
Aug. 25, 2014 (JP) ................. 2014-169993

(51) Int. Cl.
| | | |
|---|---|---|
| *G01N 1/31* | (2006.01) | |
| *G01N 15/10* | (2006.01) | |
| *G01N 15/14* | (2006.01) | |
| *G01N 33/50* | (2006.01) | |
| *G01N 35/00* | (2006.01) | |
| *G01N 33/493* | (2006.01) | |
| *G01N 33/574* | (2006.01) | |

(52) U.S. Cl.
CPC ........... *G01N 1/31* (2013.01); *G01N 15/1459* (2013.01); *G01N 33/493* (2013.01); *G01N 33/5005* (2013.01); *G01N 33/57438* (2013.01); *G01N 33/57488* (2013.01); *G01N 35/00* (2013.01); *G01N 2015/1006* (2013.01)

(58) Field of Classification Search
CPC ............. G01N 15/1459; G01N 33/493; G01N 2015/008; G01N 2015/1006; G01N 2015/1493; G01N 21/6428; G01N 21/6486; G01N 33/5005; G01N 33/5094; G01N 33/57488; G01N 35/00; C12Q 1/68; Y10T 436/11; Y10T 436/117497
USPC ............... 436/52, 63, 166, 172, 47, 800, 55; 209/582; 250/461.2; 356/336, 417; 435/34
IPC ........................ G01N 21/47,21/64, 33/48, 33/50
See application file for complete search history.

(56) References Cited

U.S. PATENT DOCUMENTS

| | | | | |
|---|---|---|---|---|
| 5,693,484 A | * | 12/1997 | Nakamoto | ............... C12Q 1/68 209/581 |
| 8,501,482 B2 | * | 8/2013 | Tanaka | ............... G01N 15/1459 436/166 |
| 9,354,161 B2 | * | 5/2016 | Sakamoto | .......... G01N 15/1434 |
| 9,417,231 B2 | * | 8/2016 | Sakamoto | ............. G01N 21/21 |
| 9,784,729 B2 | | 10/2017 | Ebi et al. | |

FOREIGN PATENT DOCUMENTS

| | | |
|---|---|---|
| CN | 101074914 A | 11/2007 |
| CN | 101173888 A | 5/2008 |
| CN | 102053057 A | 5/2011 |
| CN | 102768179 A | 11/2012 |
| CN | 103364323 | 10/2013 |
| CN | 103703367 A | 4/2014 |
| CN | 104122191 A | 10/2014 |
| EP | 0 514 178 A1 | 11/1992 |
| EP | 2 703 813 A1 | 3/2014 |
| JP | H05-322883 A | 12/1993 |
| JP | H08-240520 A | 9/1996 |
| JP | H09-329596 A | 12/1997 |
| JP | 2002-188993 A | 7/2002 |
| JP | 2009-103687 A | 5/2009 |
| JP | 2011-95182 | 5/2011 |
| JP | 2012-233754 A | 11/2012 |
| JP | 2013212058 | 10/2013 |
| WO | WO 2004/001408 A1 | 12/2003 |
| WO | WO 2006/103920 | 10/2006 |
| WO | WO 2014/133160 A1 | 9/2014 |

OTHER PUBLICATIONS

Bhatia, Alka et al. "Malignant atypical cell in urine cytology: a diagnostic dilemma", *Cytojournal, Biomed Central*, vol. 3, No. 1, 2006, pp. 1-6.

Delanghe, Joris R. et al, "The role of automated urine particle flow cytometry in clinical practice", *Clinica Chimica Acta 301*, 2000, pp. 1-18.

Sanchez-Carbayo, Marta et al., "Diagnostic Performance of the Urinary Bladder Carcinoma Antgen ELISA Test and Multiparametric DNA/Cytokeratin Flow Cytometry in Urine Voided Samples from Patients with Bladder Carcinoma", *Cancer*, vol. 92, No. 11, 2001, pp. 2811-2819.

* cited by examiner

*Primary Examiner* — Blaine Lankford
(74) *Attorney, Agent, or Firm* — Brinks Gilson & Lione

(57) ABSTRACT

Disclosed is a method for analyzing atypical cells in urine including: mixing urine, a diluent containing a surfactant, and a nucleic acid staining reagent to prepare a measurement specimen; irradiating the measurement specimen with light to detect scattered light and fluorescence light emitted from cells whose nucleic acids are stained; and detecting atypical cells contained in the measurement specimen distinguishably from white blood cells depending on a first characteristic parameter based on the scattered light and a second characteristic parameter based on the fluorescence light.

14 Claims, 24 Drawing Sheets

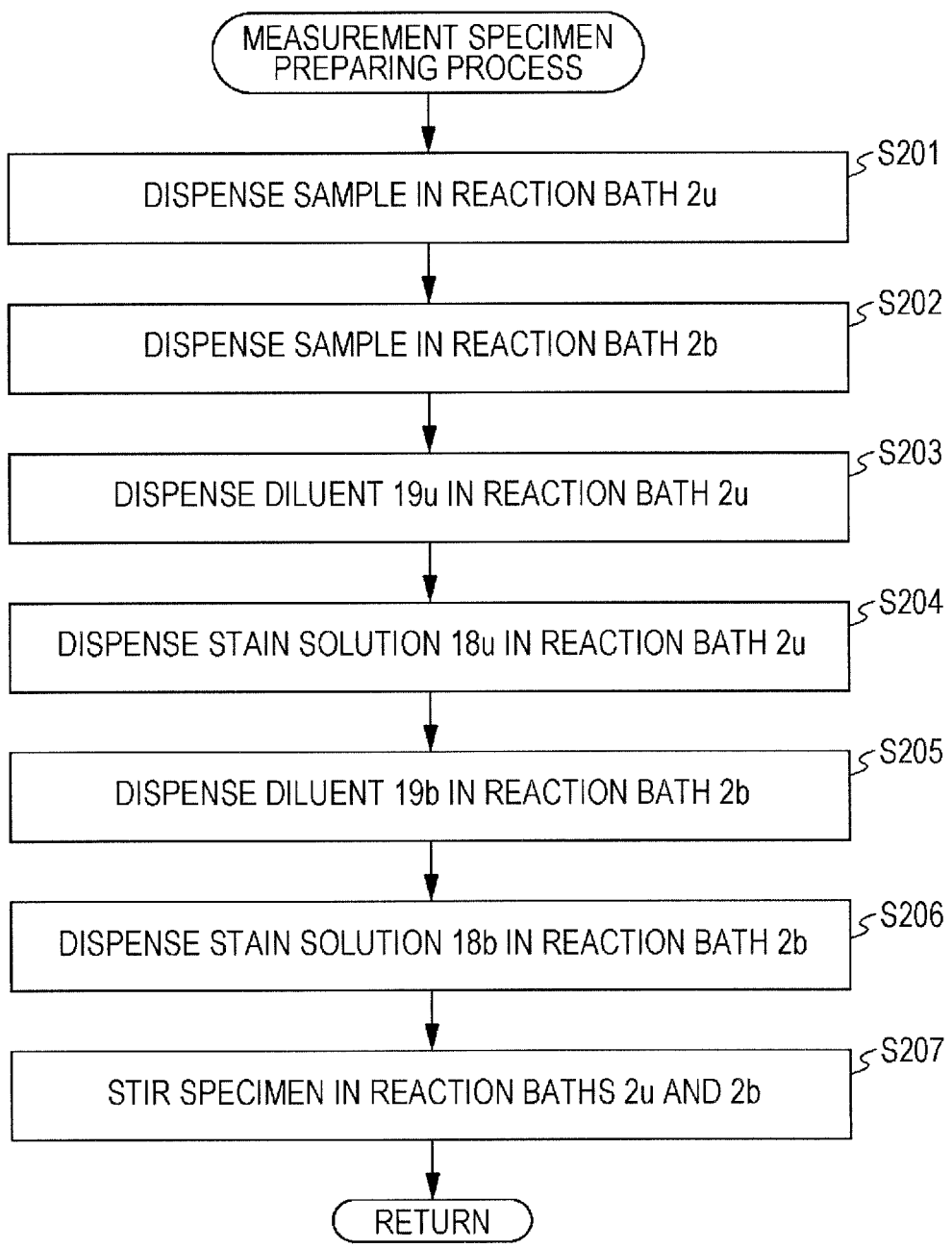

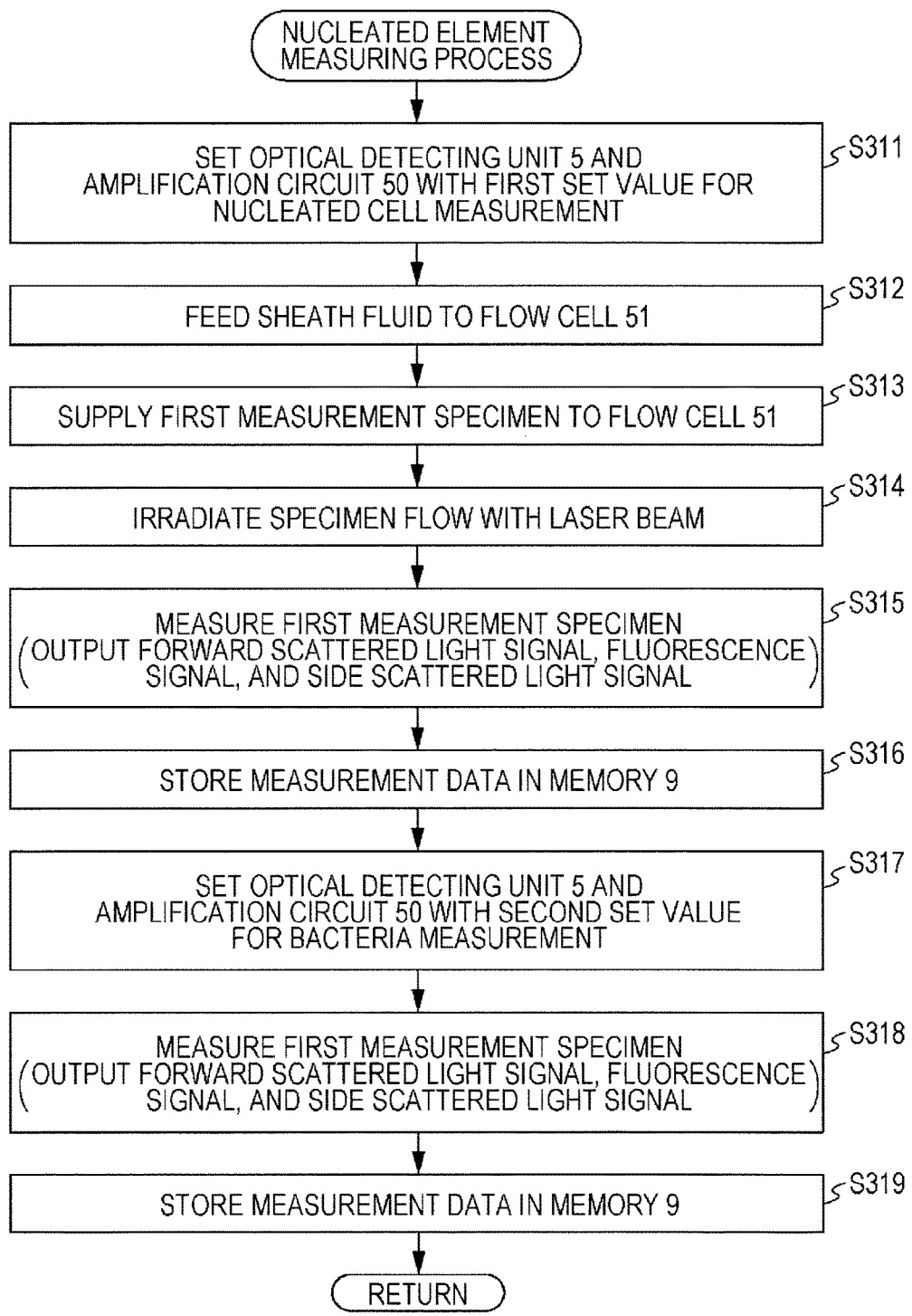

METHOD FOR ANALYZING ATYPICAL CELLS IN URINE, URINE ANALYZER, AND METHOD FOR ANALYZING ATYPICAL CELLS IN BODY FLUID

CROSS REFERENCE TO RELATED APPLICATIONS

This application claims priority from prior Japanese Patent Application No. 2014-169993, filed on Aug. 25, 2014, entitled "METHOD FOR ANALYZING ATYPICAL CELLS IN URINE, URINE ANALYZER, AND METHOD FOR ANALYZING ATYPICAL CELLS IN BODY FLUID", the entire contents of which are incorporated herein by reference.

TECHNICAL FIELD

The present invention relates to a method and a urine analyzer for analyzing atypical cells in urine by measuring a measurement specimen obtained by mixing urine and a reagent. The present invention further relates to a method for analyzing atypical cells in a body fluid by measuring a measurement specimen obtained by mixing the body fluid and a reagent.

BACKGROUND

JP 2002-188993A discloses a particle analyzer that analyzes particles in urine by flow cytometry. The particle analyzer described in JP 2002-188993A feeds a sample solution containing particles into a sheath flow cell. The particle analyzer irradiates the sheath flow cell with laser light and detects the photo-detection signals from particles. The particle analyzer classifies the particles in urine into a population that includes casts containing inclusions, epithelial cells, and close-passing white blood cells and another population based on the difference integrated value of the signal waveform of the photo-detection signals and the peak level. The particle analyzer classifies casts, epithelial cells, and close-passing white blood cells based on the pulse width of the photo-detection signals.

Atypical cells may be contained in the urine in patients with urinary tract cancer. The atypical cells which are malignant cells or cells suspected of malignancy mean cells with atypicality, such as increased nuclei due to an increase in the amount of nucleic acids or increased chromatin content. Clinically, detection of the atypical cells in the urine is very important for early detection of renal disease and urinary tract cancer.

JP 2002-188993A does not describe detecting atypical cells in urine distinguishably from other formed elements in urine.

SUMMARY OF THE INVENTION

The scope of the present invention is defined solely by the appended claims, and is not affected to any degree by the statements within this summary.

A method for analyzing atypical cells in urine, comprises: mixing urine, a diluent containing a surfactant, and a nucleic acid staining reagent to prepare a measurement specimen; irradiating the measurement specimen with light to detect scattered light and fluorescence light emitted from cells whose nucleic acids are stained; and detecting atypical cells contained in the measurement specimen distinguishably from white blood cells depending on a first characteristic parameter based on the scattered light and a second characteristic parameter based on the fluorescence light.

A urine analyzer, comprises: a specimen preparing unit that mixes urine, a first reagent for staining nucleic acid, and a diluent containing a surfactant to prepare a measurement specimen; an optical detecting unit that irradiates the measurement specimen with light and outputs a scattered light signal and a fluorescence signal depending on scattered light and fluorescence light emitted from cells whose nucleic acids are stained; and an information processing unit that detects atypical cells contained in the measurement specimen distinguishably from white blood cells based on a first characteristic parameter based on the scattered light signal and a second characteristic parameter based on the fluorescence light.

A method for analyzing atypical cells in a body fluid, comprises: mixing a body fluid other than urine and blood with a diluent containing a surfactant, and a nucleic acid staining reagent to prepare a measurement specimen; irradiating the measurement specimen with light to detect scattered light and fluorescence light emitted from cells whose nucleic acids are stained; and detecting atypical cells contained in the measurement specimen distinguishably from white blood cells depending on a first characteristic parameter reflecting a cell size based on the scattered light and a second characteristic parameter reflecting an amount of nucleic acids in cells based on the fluorescence light.

BRIEF DESCRIPTION OF THE DRAWINGS

FIG. 6 is a flow chart illustrating a procedure of a measurement specimen preparing process.

FIG. 7 is a flow chart illustrating a procedure of a nucleated component measuring process.

DETAILED DESCRIPTION OF THE PREFERRED EMBODIMENTS

Hereinafter, the preferred embodiment of the present invention will be described with reference to the drawings.
<Configuration of Urine Sample Analyzer>

In the present embodiment, a urine sample analyzer for analyzing formed elements in urine will be described. The urine sample analyzer according to the present embodiment retrieves the urine sample inside, and analyzes formed elements in urine (such as red blood cells, white blood cells, epithelial cells, casts, bacteria, atypical cells or white blood cell clumps).

Figure 1:
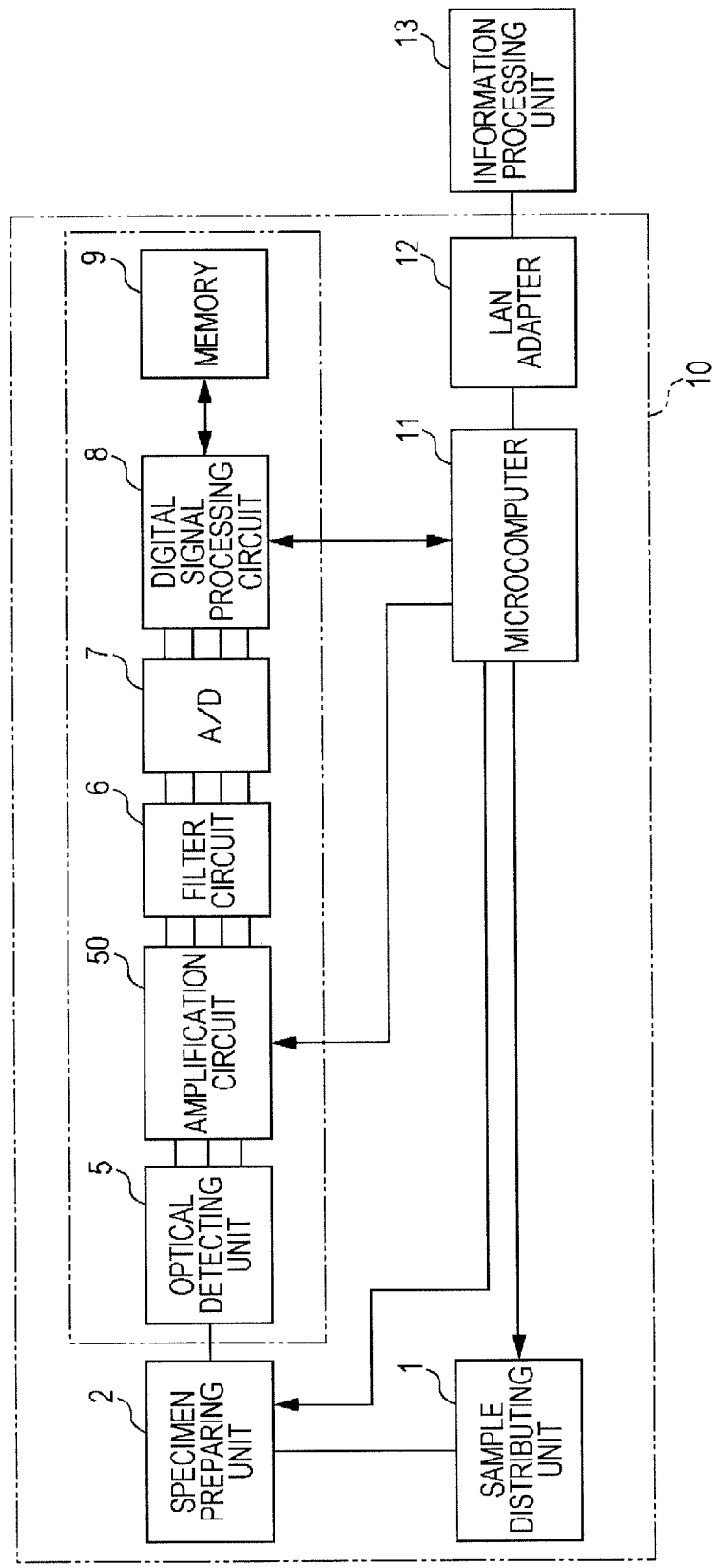
FIG. 1 is a block diagram illustrating a configuration of a urine sample analyzer according to an embodiment.

The configuration of the urine sample analyzer will be described with reference to FIG. 1. A urine sample analyzer 100 comprises a measuring unit 10 and an information processing unit 13. The measuring unit 10 includes a sample distributing unit 1 that aspirates a urine sample from a test tube, and divides the aspirated sample into two aliquots, a specimen preparing unit 2 that prepares a measurement specimen, and an optical detecting unit 5 that detects information on formed elements from the measurement specimen.

Figure 2:
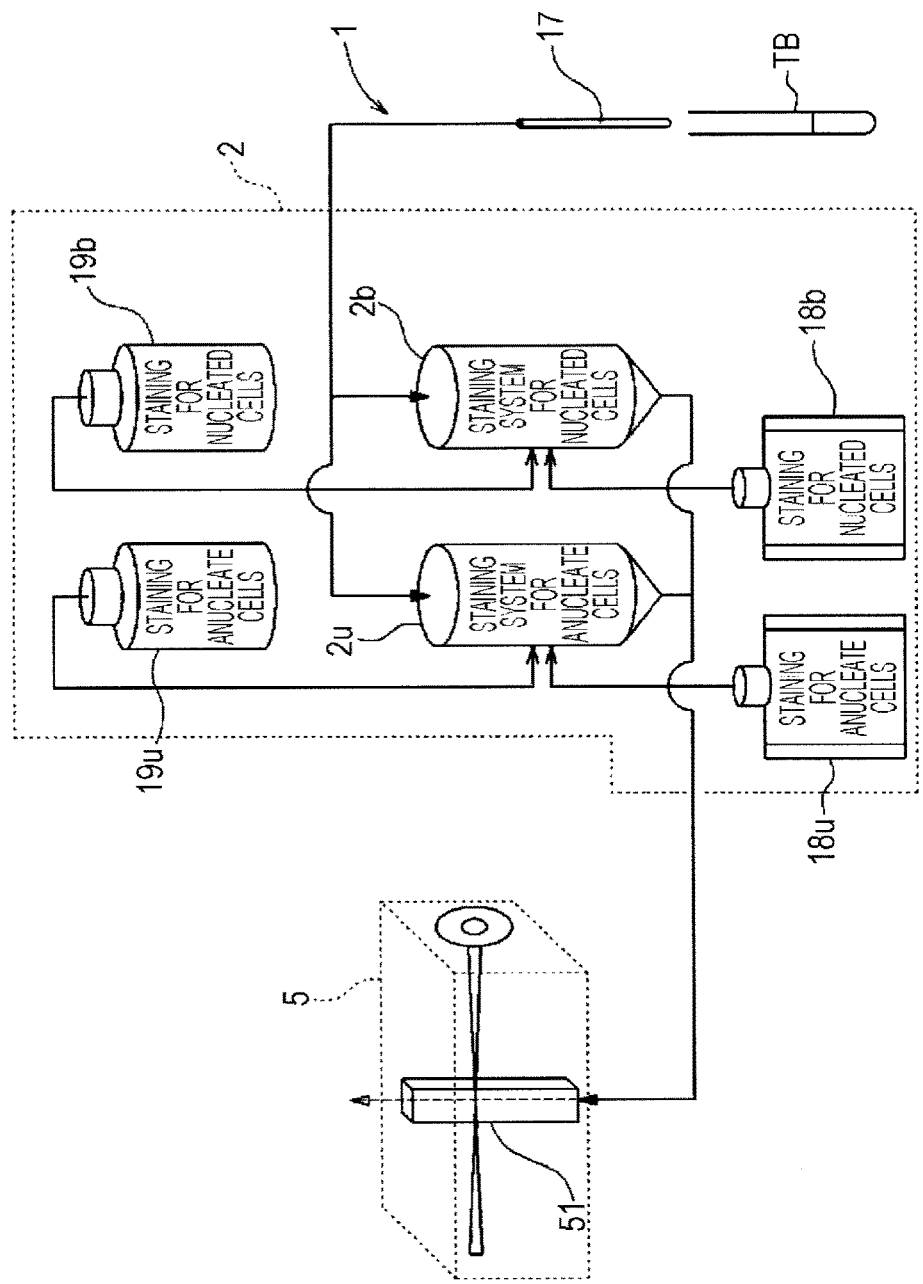
FIG. 2 is a view illustrating an outline functional configuration of a specimen preparing unit and an optical detecting unit.

As shown in FIG. 2, the sample distributing unit 1 includes an aspirating tube 17 and aspirates the urine sample in a test tube TB through the aspirating tube 17. The specimen preparing unit 2 includes a reaction bath 2u and a reaction bath 2b. The sample distributing unit 1 quantitatively distributes aliquots of the urine sample to each of the reaction bath 2u and the reaction bath 2b.

The specimen preparing unit 2 mixes the distributed aliquot, a diluent 19b, and a stain solution 18b in the reaction bath 2b. Thus, the formed elements in the urine sample are stained with the dye in the stain solution 18b. The mixture prepared in the reaction bath 2b is used to analyze nucleated cells in urine, such as white blood cells, epithelial cells, fungi, bacteria or atypical cells. Hereinafter, the mixture prepared in the reaction bath 2b is referred to as "first measurement specimen".

The specimen preparing unit 2 mixes the distributed aliquot, a diluent 19u, and a stain solution 18u in the reaction bath 2u. Thus, the formed elements in the urine sample are stained with the dye in the stain solution 18u. The mixture prepared in the reaction bath 2u is used to analyze anucleate particles in urine such as red blood cells or casts. Hereinafter, the mixture prepared in the reaction bath 2u is referred to as "second measurement specimen".

The optical detecting unit 5 includes a flow cell 51. The reaction baths 2u and 2b are connected by the flow cell 51 and a tube. The measurement specimen prepared in the reaction baths 2u and 2b can be supplied to the flow cell 51. The second measurement specimen in the reaction bath 2u is first supplied to the optical detecting unit 5 and then the first measurement specimen in the reaction bath 2b is supplied to the optical detecting unit 5. The flow cell 51 forms a narrow flow of the supplied first and second measurement specimens which are enveloped with the sheath fluid. The flow of the first and second measurement specimens in the flow cell 51 is irradiated with laser light. Such operation is automatically carried out by operating a pump and an electromagnetic valve (not shown) according to the control of a microcomputer 11 illustrated in FIG. 1.

The stain solution 18b contains a dye for staining nucleic acid. More particularly, the stain solution 18b contains an intercalator for specifically staining nucleic acid and a fluorescent dye which binds to a minor groove. Examples of the intercalator include known cyanine dyes, acridine dyes, and phenanthridium dyes. Examples of the cyanine intercalator include SYBR Green I and Thiazole orange. Examples of the acridine intercalator include Acridin orange. Examples of the phenanthridium intercalator include propidium Iodide and Ethidium bromide. Examples of a dye that binds to a minor groove include known dyes such as DAPI and Hoechst. Examples of a dye that binds to a minor groove of Hoechet include Hoechst 33342 and Hoechst 33258. In the embodiment, the cyanine intercalator is preferred. Particularly, SYBR Green I and Thiazole orange are preferred.

The diluent 19b contains a surfactant. More particularly, the diluent 19b contains a cationic surfactant for enhancing passage of the stain solution 18b through a membrane by damaging the cell membrane, hemolyzing red blood cells and shrinking contaminants such as red blood cell debris. The type of surfactant is not limited to the cationic surfactant and may be a nonionic surfactant. When the urine sample, the stain solution 18b, and the diluent 19b are mixed, the nucleated formed elements in urine are stained depending on the configuration and characteristics.

Since the diluent 19b contains the surfactant, red blood cells in the second measurement specimen are hemolyzed, and nucleated cells such as white blood cells can be measured at high accuracy. The use of the diluent 19b containing a surfactant gives damage to the cell membrane, whereby staining of nucleic acid can be efficiently carried out. This also contributes to improvement in measurement accuracy of cells having nucleic acids.

The stain solution 18u contains a fluorescent dye for staining formed elements not containing nucleic acids.

The diluent 19u is a reagent containing a buffer as its main component. The diluent 19u contains an osmotic pressure compensating agent for the purpose of preventing red blood cells hemolysis and for the purpose of obtaining stable fluorescence intensity.

Figure 3:
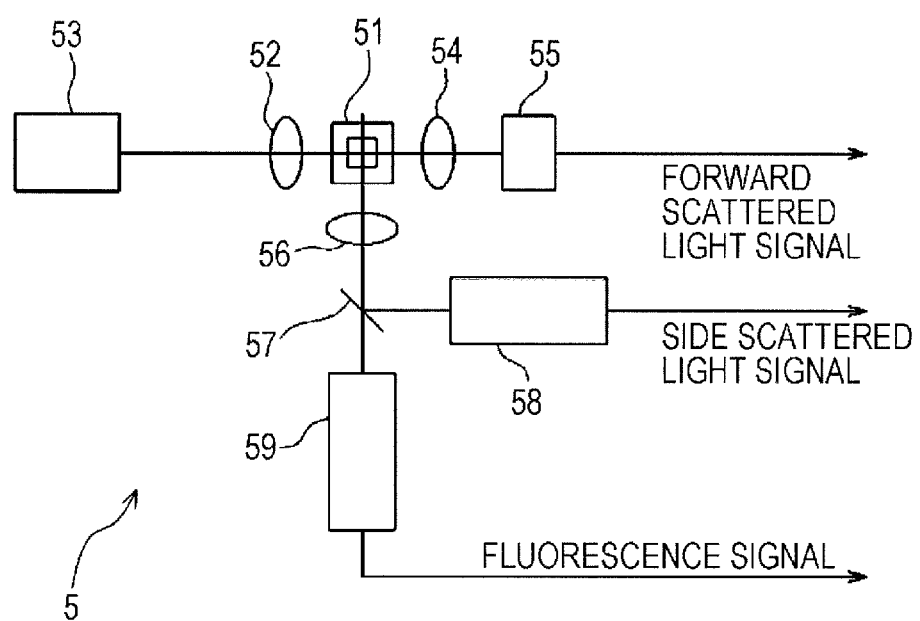
FIG. 3 is a view illustrating a configuration of an optical detecting unit.

The configuration of the optical detecting unit 5 will be described with reference to FIG. 3. The optical detecting unit 5 includes a flow cell 51, a condenser lens 52, a semiconductor laser light source 53, a light collecting lens 54, a first scattered light detector 55, a light collecting lens 56, a dichroic mirror 57, a second scattered light detector 58, and a fluorescence light detector 59.

The condenser lens 52 condenses the laser light emitted from the light source 53 and forms a flat beam spot on the specimen flow in the flow cell 51. The diameter of the beam spot in the specimen flow direction is from 3 µm to 8 µm. In order to stably irradiate the cell nucleus with laser light, the diameter of the beam spot in the flow direction is preferably from 3.5 µm to 7.5 µm, more preferably from 4 µm to 7 µm. The diameter of the beam spot in the flow direction according to the embodiment is from 4 µm to 7 µm.

The light collecting lens 54 collects the forward scattered light emitted from the formed elements in the measurement specimen and directs the collected light to the first scattered light detector 55. The light collecting lens 56 collects the side scattered light and fluorescent light emitted from the formed elements and directs the collected light to the dichroic mirror 57. The dichroic mirror 57 reflects the side scattered light toward the second scattered light detector 58 as a photomultiplier and transmits the fluorescence light toward the fluorescence light detector 59 as a photomultiplier.

Each of the first scattered light detector 55, the second scattered light detector 58, and the fluorescence light detector 59 converts the received light signal to an electric signal, and outputs the forward scattered light signal (hereinafter referred to as "FSC"), the side scattered light signal (hereinafter referred to as "SSC"), and the fluorescence signal (hereinafter referred to as "FL"). The FSC is a signal that indicates a temporal change of the intensity of the forward scattered light, the SSC is a signal that indicates a temporal change of the intensity of the side scattered light, and the FL is a signal that indicates a temporal change of the intensity of the fluorescent light. The fluorescence light detector 59 outputs fluorescence signal in a low sensitivity and in a high sensitivity by switching a drive voltage supplied to it. The switching of the sensitivity is carried out by the microcomputer 11 illustrated in FIG. 1.

Referring back to FIG. 1, the configuration of the urine sample analyzer 100 will be described. The measuring unit 10 comprises an amplification circuit 50 that amplifies the output signal of the optical detecting unit 5, a filter circuit 6 that filters the output signal from the amplification circuit 50, an A/D converter 7 that converts the output signal (analog signal) of the filter circuit 6 to a digital signal, a digital signal processing circuit 8 that subjects the digital signal to a predetermined waveform processing, a memory 9 connected to the digital signal processing circuit 8, the microcomputer 11, and a LAN adapter 12.

The optical detecting unit 5, the amplification circuit 50, the filter circuit 6, the A/D converter 7, the digital signal processing circuit 8, and the memory 9 configure a measurement unit 10a that measures the measurement specimen and generates measurement data.

In the optical detecting unit 5, each of the FSC, SSC, and FL is amplified by a preamplifier. Each of the amplified signals is input to the amplification circuit 50. The FL signal channel extended from the output side of the optical detecting unit 5 is branched into two signal channels between the preamplifier and the amplification circuit 50. One of the signal channels is connected to an amplifier with a high amplification factor (High-AMP) of the amplification circuit 50. The other signal channel is connected to an amplifier with a low amplification factor (Low-AMP). Therefore, the FLH amplified with high sensitivity and the FLL amplified with low sensitivity are taken out from the FL corresponding to one particle. Hereinafter, the FL input to the High-AMP is referred to as "FLH", and the FL input to the Low-AMP is referred to as "FLL".

The amplification circuit 50 amplifies four types of signals: the FSC; SSC; FLH; and FLL according to the set gain. The amplification circuit 50 can set a plurality of different gains. The microcomputer 11 sets the gain of the amplification circuit 50 so that the sensitivity of the amplification circuit 50 can be adjusted.

The information processing unit 13 is connected to the measuring unit 10 with a LAN cable through the LAN adapter 12.

Figure 4:
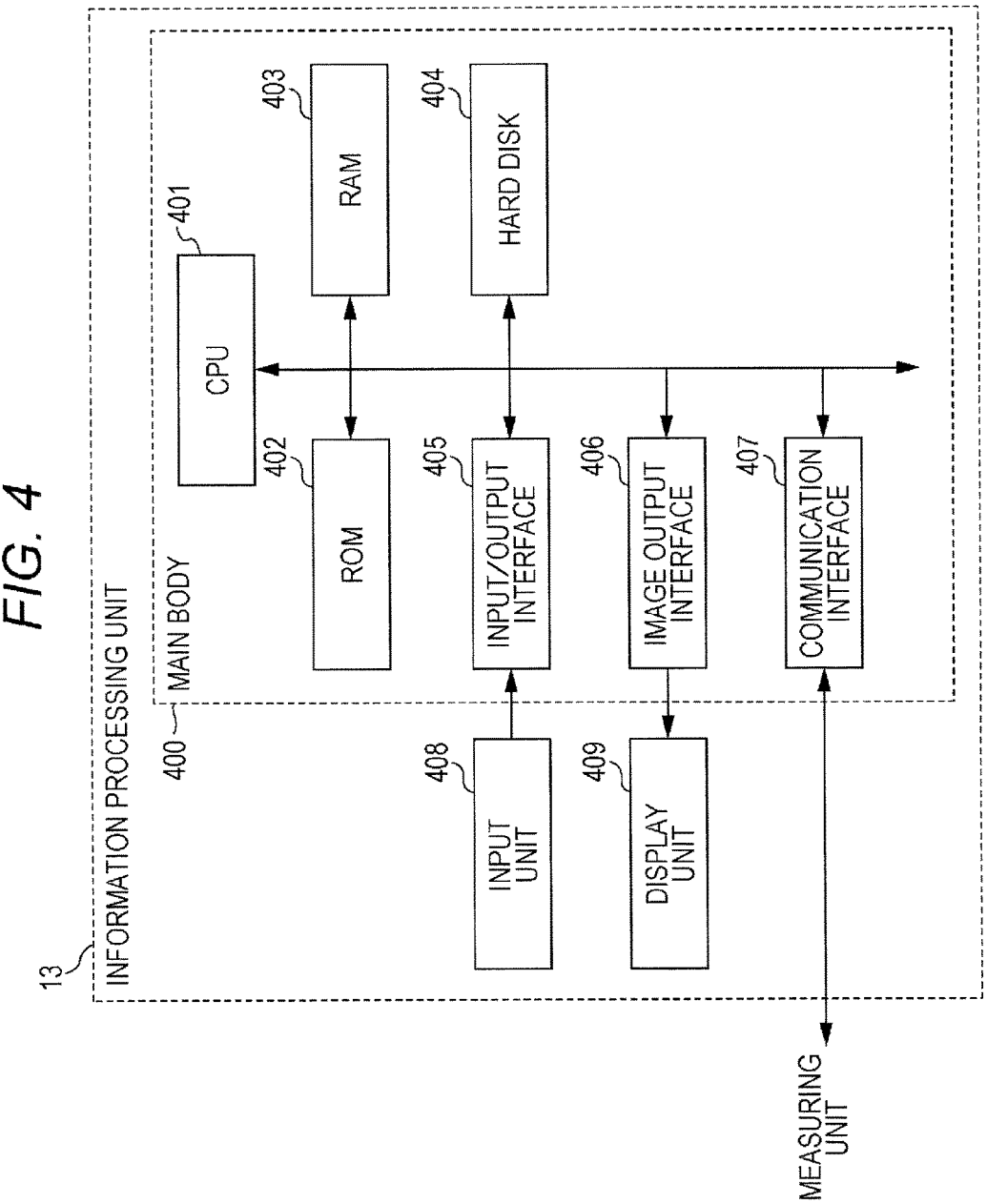
FIG. 4 is a block diagram illustrating a configuration of an information processing unit.

FIG. 4 illustrates a configuration of the information processing unit 13. The information processing unit 13 is a personal computer. The information processing unit 13 comprises a main body 400, an input unit 408, and a display unit 409. The main body 400 includes a CPU 401, a ROM 402, a RAM 403, a hard disk 404, an input/output interface 405, an image output interface 406, and a communication interface 407.

The CPU 401 executes a computer program stored in the ROM 402 and a computer program loaded with the RAM 403. The RAM 403 is used to read out the computer programs stored in the ROM 402 and the hard disk 404. The RAM 403 is utilized as a work area when the CPU 401 executes these computer programs.

The hard disk 404 is installed with the computer program for analyzing the measurement data provided from the measuring unit 10 and outputting the analysis result.

The input unit 408 is connected to the input/output interface 405. The display unit 409 is connected to the image output interface 406. The measuring unit 10 is connected to the communication interface 407, and is data communicably connected to the information processing unit 13.

<Operation of Urine Sample Analyzer>

Hereinafter, the operation of the urine sample analyzer according to the embodiment will be described.

Figure 5:
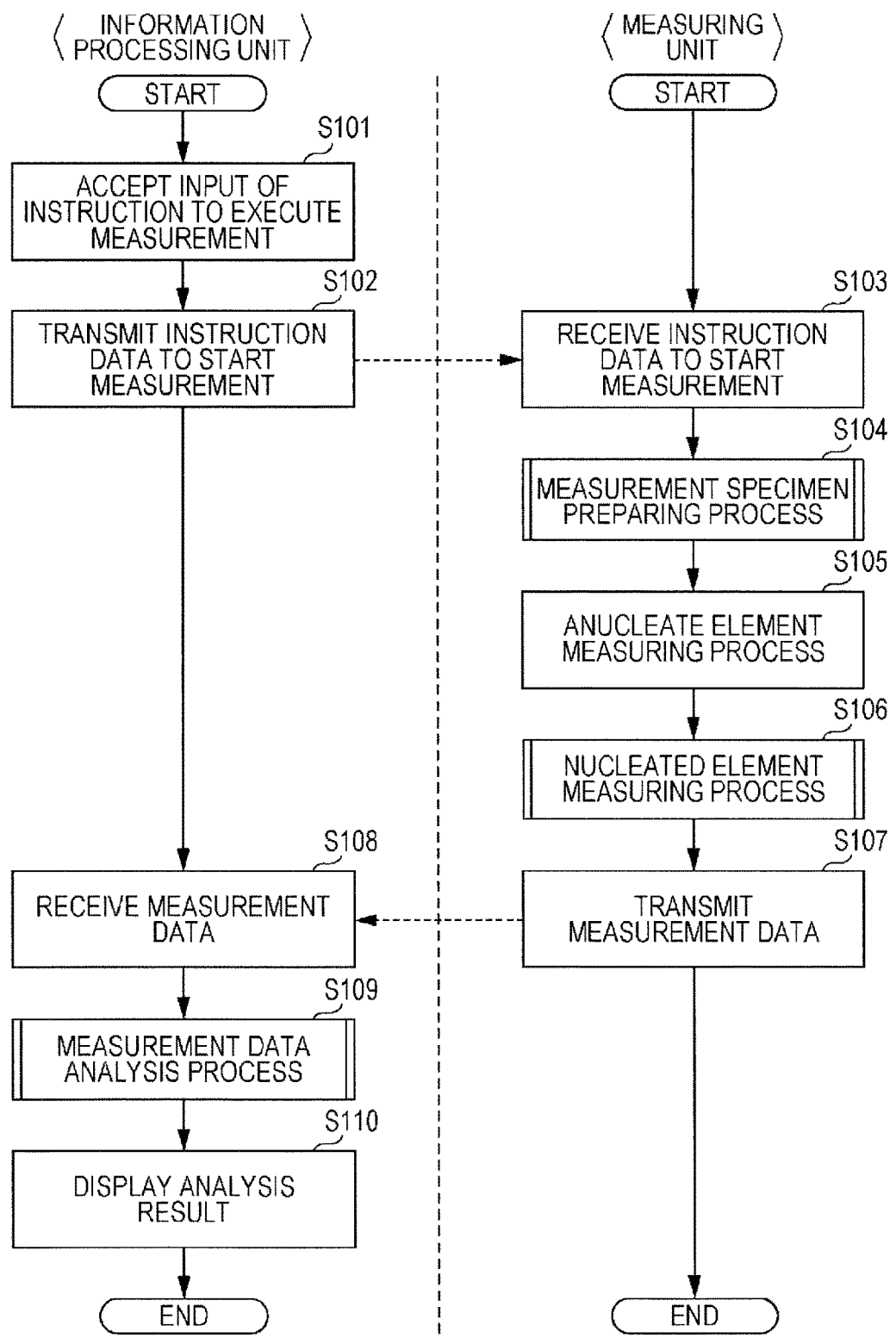
FIG. 5 is a flow chart illustrating a procedure of a sample measurement process.

A urine sample measuring process of the urine sample analyzer 100 will be described with reference to a flow chart of FIG. 5. First, in Step 101, when a user inputs an instruction to execute the measurement to the input unit 408, the CPU 401 of the information processing unit 13 receives the instruction. Upon receiving such instruction, the CPU 401 transmits the instruction data instructing the start of measurement to the measuring unit 10 in Step S102. In Step S103, the measuring unit 10 receives the instruction data.

The microcomputer 11 executes a measurement specimen preparing process in Step S104, an anucleate element measuring process in Step S105, and a nucleated element measuring process in Step S106.

The measurement specimen preparing process will be described with reference to FIG. 6. In the measurement specimen preparing process, the microcomputer 11 first controls the sample distributing unit 1 to cause the aspirating tube 17 to aspirate a predetermined amount of urine sample from the test tube TB and dispense aliquots of the predetermined amount of urine sample to the reaction bath 2u and the reaction bath 2b in Steps S201 and S202.

The microcomputer 11 controls the specimen preparing unit 2 to execute the following Steps S203 to S207. A predetermined amount of the diluent 19u and the stain solution 18u are quantified and dispensed to the reaction bath 2u in Steps S203 and S204. A predetermined amount of the diluent 19b and the stain solution 18b are quantified and dispensed to the reaction bath 2b in Steps S205 and S206. The reaction bath 2u and the reaction bath 2b are warmed to a predetermined temperature by a heater (not shown). The mixture of dispensed diluent and stain solution in each of the reaction baths is stirred with a stirring tool (not shown) such as a propeller in Step S207 in the warmed state. As a result of the operation of Steps S201 to S207, a second measurement specimen for measuring anucleate element is prepared in the reaction bath 2u and a first measurement specimen for measuring nucleated element is prepared in the reaction bath 2b. After the process of Step S207 is finished, the microcomputer 11 returns the process to the main routine.

Subsequently, the anucleate element measuring process will be described. In the anucleate element measuring process, the sheath fluid and the second measurement specimen are supplied from the reaction bath 2u to the flow cell 51. In the flow cell 51, a specimen flow of the second measurement specimen enveloped by the sheath fluid is formed. The formed specimen flow is irradiated with the laser beam from the light source 53, and a beam spot is formed in the flow cell 51. When a particle passes the beam spot, forward scattered light, fluorescence light, and side scattered light are generated. The forward scattered light, the fluorescence light, and the side scattered light are respectively received by the first scattered light detector 55, the fluorescence light detector 59, and the second scattered light detector 58, converted to the electric signals, and output as FSC, FLH, FLL, and SSC. The output FSC, FLH, FLL, and SSC are amplified by the amplification circuit 50.

The FSC, FLH, FLL, and SSC amplified by the amplification circuit 50 are filtered by the filter circuit 6, converted into digital signals by the A/D converter 7, and signal-processed by the digital signal processing circuit 8. Accordingly, when a particle passes the flow cell 51, analysis parameters such as forward scattered light intensity (FSCP), forward scattered light pulse width (FSCW), fluorescence intensity (FLHP), fluorescence light pulse width (FLLW), side scattered light intensity (SSCP) are extracted. The analysis parameters are stored in the memory 9 as measurement data, and the anucleate element measuring process is finished.

Subsequently, the nucleated element measuring process will be described with reference to FIG. 7. In the nucleated element measuring process, the microcomputer 11 first sets the sensitivities of the first scattered light detector 55, the second scattered light detector 58, and the fluorescence light detector 59 and the gain of the amplification circuit 50 at the first set value in Step 311. The first set value is a set value for measuring nucleated cells with nuclei, larger than bacteria, such as white blood cells, epithelial cells, and fungi. The microcomputer 11 causes a compressor (not shown) to feed the sheath fluid to the flow cell 51 in Step 312. The microcomputer 11 causes a compressor (not shown) to supply the first measurement specimen from the reaction bath 2b to the flow cell 51 while the supply of sheath fluid to the flow cell 51 is continued in Step S313.

After such operation, a specimen flow of the first measurement specimen enveloped by the sheath fluid is formed in the flow cell 51. The formed specimen flow is irradiated with the laser beam from the light source 53, and a beam spot is formed in the flow cell 51 in Step S314. When a particle passes the beam spot, forward scattered light, fluorescence light, and side scattered light are generated. The forward scattered light, the fluorescence light, and the side scattered light are respectively received by the first scattered light detector 55, the fluorescence light detector 59, and the second scattered light detector 58 and converted to the electric signals in Step S315. The sensitivity when the fluorescence light detector 59 converts the electric signals to light receiving levels is determined by the first set value for measuring nucleated cells in Step S311.

The electric signals corresponding to the light receiving levels of the first scattered light detector 55, the fluorescence light detector 59, and the second scattered light detector 58 are output as FSC, FL, and SSC. The optical detecting unit 5 divides the FL into two signals: FLH and FLL and outputs the signals to the amplification circuit 50. The input signals are amplified by the amplification circuit 50. The amplification factor of the signal by the amplification circuit 50 is determined by the first set value for measuring nucleated cells in Step S311.

The sensitivity of the first set value is lower than the sensitivity of the second set value as described later. In other words, when the first set value is set, the FL is amplified at the amplification factor lower than the amplification factor when the second set value is set. Specifically, when the first set value is set, the fluorescence light detector 59 photoelectrically converts and outputs the fluorescence light emitted from particles at a low sensitivity. The FLH and FLL output from the optical detecting unit 5 are respectively amplified at a low amplification factor and a high amplification factor by the High-AMP and the Low-AMP of the amplification circuit 50. As a result, two types of fluorescence signals: a fluorescence signal (FLL) with low sensitivity amplified at a low amplification factor and a first fluorescence signal with high sensitivity amplified at a high amplification factor (hereinafter referred to as "FLH1") are obtained.

The amplified FSC, FLL, FLH1, and SSC are filtered by the filter circuit 6, converted into digital signals by the A/D converter 7, and subjected to a predetermined signal process by the digital signal processing circuit 8.

The digital signal processing circuit 8 extracts parameters used for the analysis process from optical signals (FSC, SSC, FLL, FLH1) by the signal process. The analysis parameters include forward scattered light intensity (hereinafter referred to as "FSCP"), forward scattered light pulse width (hereinafter referred to as "FSCW"), side scattered light intensity (hereinafter referred to as "SSCP"), fluorescence intensity with low sensitivity (hereinafter referred to as "FLLP"), fluorescence light pulse width with low sensitivity (hereinafter referred to as "FLLW"), fluorescence pulse area with low sensitivity (hereinafter referred to as "FLLA"), first fluorescence intensity with high sensitivity (hereinafter referred to as "FLHP1"), first fluorescence light pulse width with high sensitivity (hereinafter referred to as "FLHW1"), first fluorescence light pulse area with high sensitivity (hereinafter referred to as "FLHA1"), forward scattered light difference integrated value-peak level ratio (hereinafter referred to as "FSC-DS/P"), and fluorescence light (with low sensitivity) difference integrated value-peak level ratio (hereinafter referred to as "FL-DS/P").

On the basis of FIGS. 8A to 8D, the extraction of analysis parameters will be described. The analysis parameters include three types of "intensity", "pulse width", and "pulse area" regarding each of the optical signals. P represents the intensity, W represents the pulse width, and A represents the pulse area.

Figure 8A:
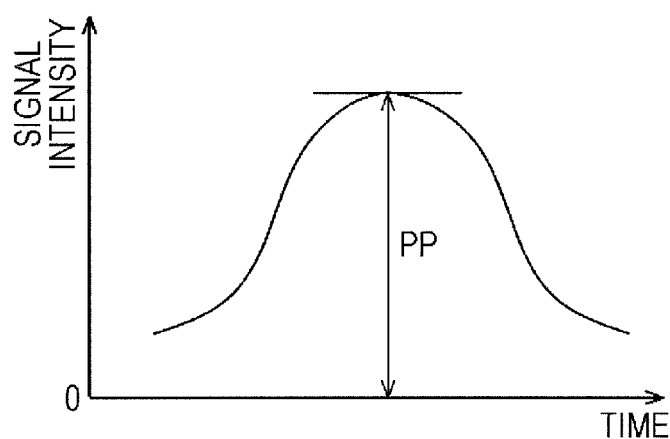
FIG. 8A is a pattern diagram to explain the intensity of an optical signal.
Figure 8B:
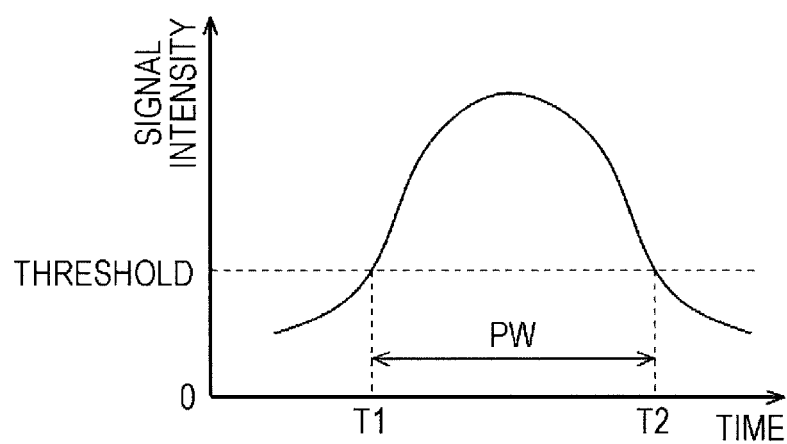
FIG. 8B is a pattern diagram to explain the pulse width of the optical signal.
Figure 8C:
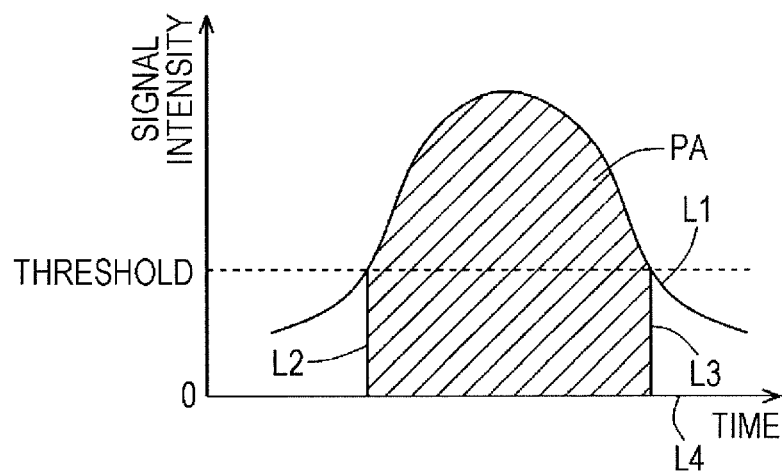
FIG. 8C is a pattern diagram to explain the pulse area of the optical signal.

The intensity of each of the optical signals, such as FSCP, SSCP, FLLP, and FLHP1 is obtained as a pulse peak height PP as illustrated in FIG. 8A. The pulse width of each of the optical signals, such as FSCW, FLLW, and FLHW1 is obtained as an interval PW between a time T1 when the pulse exceeds a predetermined threshold and a time T2 when the pulse is less than the threshold as illustrated in FIG. 8B. The pulse area of each of the optical signals, such as FLLA and FLHA1 is obtained as an area of a region PA (a shaded region in the figure) which is surrounded by a pulse shape line L1 of the signal, straight lines L2 and L3 representing the time when the height of the pulse is a predetermined threshold, and a straight line L4 representing an optical signal intensity value of 0, i.e., a time integration value of the signal intensity as illustrated in FIG. 8C.

The method for extracting analysis parameters described above is only an example, and different extraction methods may be used. The pulse area may be an approximate value as long as it is a value reflecting the area under the pulse time curve. The pulse area is not limited to the time integration value. For example, the pulse area may be a product of the pulse width and the peak height or may be a triangular area calculated from the pulse width and the peak height. In the form of extracting the time integration value, the base may not be the straight line representing an intensity of 0, and can be appropriately determined. For example, the base may be a predetermined threshold illustrated in FIG. 8C or a pulse value when only the sheath fluid is fed to the flow cell 51 as a standard value.

Figure 8D:
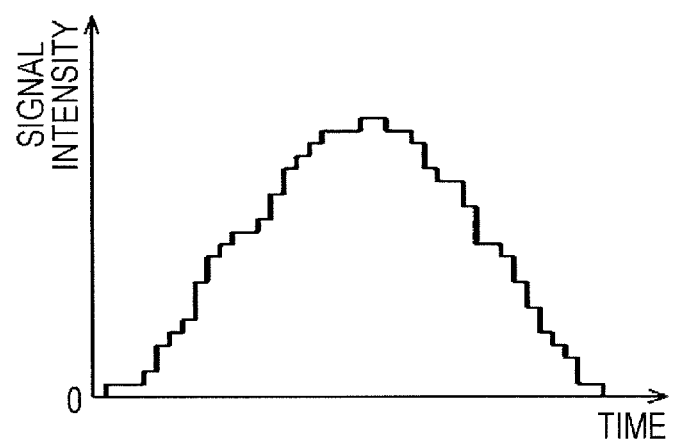
FIG. 8D is a pattern diagram to explain the difference integrated value of the pulse of the optical signal.

Subsequently, FSC-DS/P and FL-DS/P will be described. The difference integrated value is a value calculated by time-differentiating the signal waveform and adding absolute values of respective differential values. Since the optical signal is a discrete time signal, the difference integrated value is a value calculated by adding absolute values in difference between adjacent signal values. In FIG. 8D, the difference between adjacent signal values is indicated by a thick line. The difference integrated value-peak level ratio (hereinafter referred to as "DS/P") is a value calculated by dividing the difference integrated value of pulse in an optical signal by a peak value of the pulse.

Figure 9A:
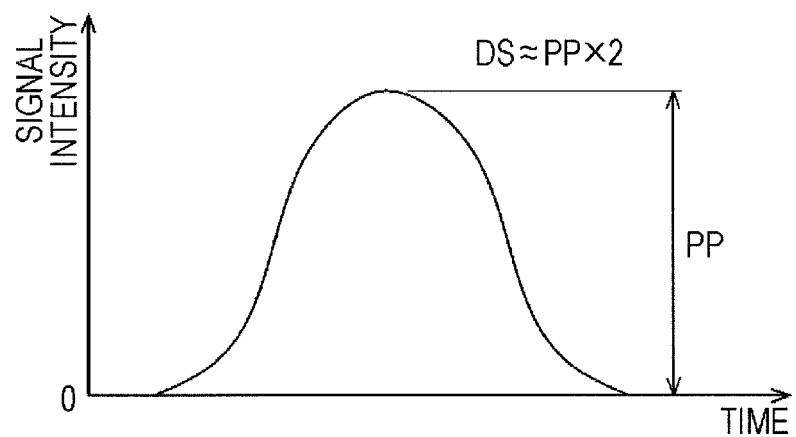
FIG. 9A is a pattern diagram to explain the difference integrated value in a monophasic pulse.
Figure 9B:
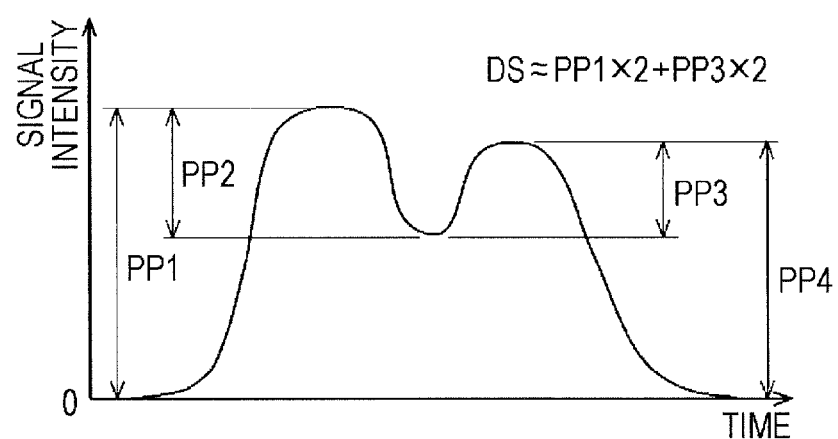
FIG. 9B is a pattern diagram to explain the difference integrated value in a multiphasic pulse.

As illustrated in FIG. 9A, the pulse in the optical signal is a monophasic pulse. Namely, in the case of a pulse waveform having no recess, the difference integrated value approximates to a value PP×2 calculated by doubling the pulse peak value PP. On the other hand, as illustrated in FIG. 9B, when the pulse in the optical signal is a multiphasic pulse (i.e., in the case of a pulse waveform having recess), the difference integrated value is larger than the value calculated by doubling the pulse peak value. In the example of FIG. 9B, the difference integrated value is calculated by a sum of PP1, PP2, PP3, and PP4, and approximates to PP1×2+PP3×2. Thus, the difference integrated value is larger than the value PP1×2 calculated by doubling the peak value. Therefore, the DS/P is almost a constant value when the pulse in the optical signal is the monophasic pulse. In the case of the multiphasic pulse, the DS/P is a value larger than that in the case of the monophasic pulse. Hence, the DS/P is information for indicating whether the pulse in the optical signal is monophasic or multiphasic.

Refer to FIG. 7 again. The characteristic parameters are extracted from the optical signal by the digital signal processing circuit 8. The characteristic parameters are stored as measurement data in the memory 9 in Step S316.

When a predetermined time passes after the first measurement specimen is supplied to the flow cell 51, the microcomputer 11 changes the sensitivity of the fluorescence light detector 59 and the gain of the amplification circuit 50 into the second set value in Step S317. The second set value is a set value for measuring bacteria.

In a state where the fluorescence light detector 59 and the amplification circuit 50 are set at the second set value, the microcomputer 11 executes a measurement process of the first measurement specimen by the measurement unit 10a in Step S318. When the first measurement specimen is measured, FL is output from the fluorescence light detector 59 at the sensitivity determined by the second set value. The output signals of the first scattered light detector 55, the second scattered light detector 58, and the fluorescence light detector 59 are amplified by the amplification circuit 50 at the amplification factor determined by the second set value.

The second set value is a set value for amplifying FL with high sensitivity compared to the first set value. In other words, when the second set value is set, the FL is amplified at a high amplification factor as compared to when the first set value is set. When the second set value is set, the sensitivity of the received light photoelectrically converted by the fluorescence light detector 59 is set to several times the first set value. The amplification factor of the amplification circuit 50 is the same as the amplification factor in the first set value. In a state where the second set value is set, the FL output from the fluorescence light detector 59 is amplified by the High-AMP of the amplification circuit 50, and a second fluorescence signal with high sensitivity (hereinafter referred to as "FLH2") is obtained.

The received light sensitivity of the fluorescence light detector 59 in the second set value is 5 times the received light sensitivity of the fluorescence light detector 59 in the first set value. This is because bacteria have a small size compared to nucleated cells (e.g., white blood cells and epithelial cells) and has a small amount of fluorescence compared to nucleated cells. The sensitivity of the fluorescence light detector 59 is increased to a level higher than the case of the nucleated cell measurement so that the sensitivity becomes suitable for bacteria. It enables bacteria to be detected at high accuracy. In the embodiment, in order to quintuple the amplification factor in the second set value, only the sensitivity of the fluorescence light detector 59 is increased. The same effect can be obtained by adjusting the gain of the fluorescence light detector 59 and the gain of the amplification circuit 50 and making the whole amplification factor to 5 times the amplification factor of the first set value. For example, in the second set value, the sensitivity of the fluorescence light detector 59 may be increased to 2.5 times the sensitivity in the first set value, and the amplification factor by the amplification circuit 50 may be increased to twice the amplification factor in the first set value.

The amplified FSC, FLH2, and SSC are filtered by the filter circuit 6, converted into digital signals by the A/D converter 7, and subjected to a predetermined signal process by the digital signal processing circuit 8. After the signal process, FSCP and FSCW are extracted from the FSC. SSCP is extracted from the SSC. A peak value of FLH2 is extracted as a second fluorescence intensity with high sensitivity (hereinafter referred to as "FLHP2"). A pulse width of the FLH2 is extracted as a second fluorescence light pulse width with high sensitivity (hereinafter referred to as "FLHW2"). A pulse area of the FLH2 is extracted as a second fluorescence light pulse area with high sensitivity (hereinafter referred to as "FLHA2"). As described above, analysis parameters of each of the particles passed through the flow cell 51 are obtained.

The digital signal processing circuit 8 stores data of the parameters extracted for each particle as measurement data in the memory 9 in Step S319. After the process described above is completed, the microcomputer 11 returns the process to the main routine.

Refer to FIG. 5 again. After the nucleated element measuring process, the microcomputer 11 transmits the measurement data generated by the anucleate element measuring process and the nucleated element measuring process to the information processing unit 13 in Step S107, and terminates the process.

After the information processing unit 13 receives the measurement data in Step S108, the CPU 401 executes a measurement data analysis process generates an analysis result of the urine sample, and stores the analysis result in the hard disk 404.

Figure 10:
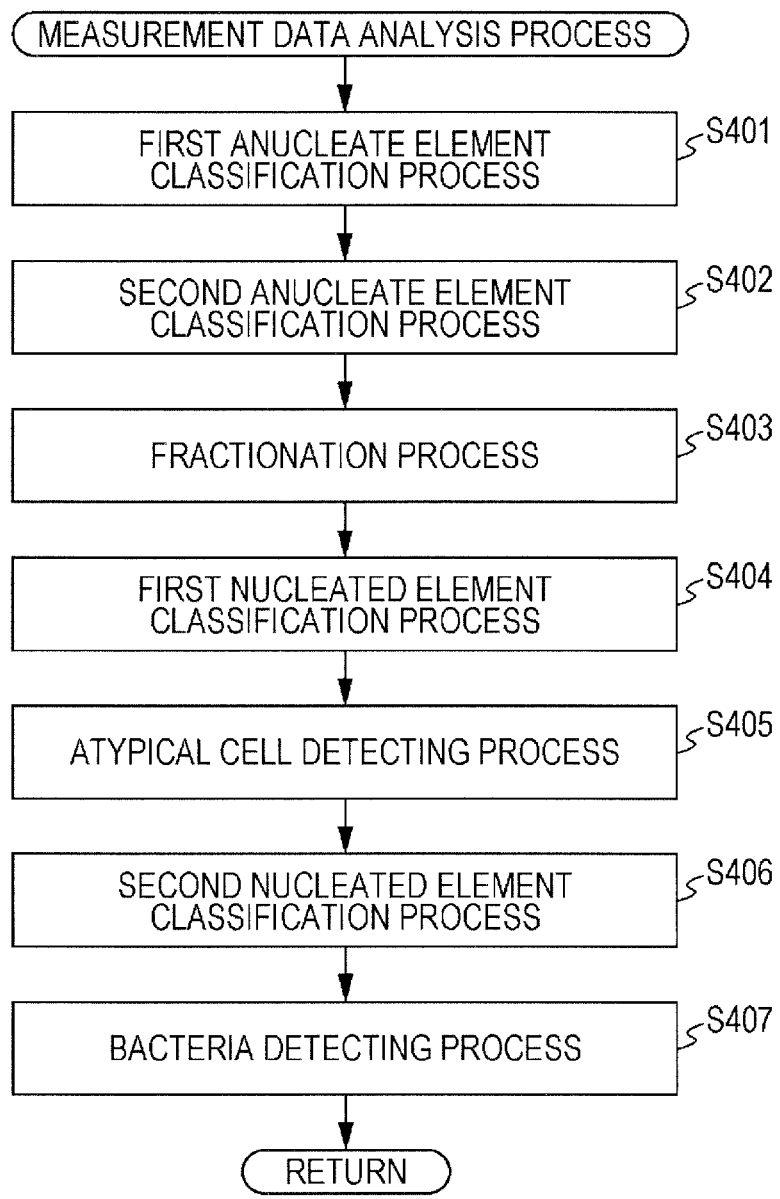
FIG. 10 is a flow chart illustrating a procedure of a measurement data analysis process.

The measurement data analysis process will be described with reference to FIG. 10. The measurement data analysis process includes a first anucleate element classification process in Step S401, a second anucleate element classification process in Step S402, a fractionation process in Step S403, a first nucleated element classification process in Step S404, an atypical cell detecting process in Step S405, a second nucleated element classification process in Step S406, and a bacteria detecting process in Step S407.

In the first anucleate element classification process S401, red blood cells and crystals are detected using the FSC and FLH obtained by measuring the second measurement specimen, and the counted values thereof are determined.

In the second anucleate element classification process S402, casts and mucus threads are detected using the FSC and FLL obtained by measuring the second measurement specimen, and the counted values thereof are determined.

Further, cells having nucleic acids in the urine sample are classified by the fractionation process, the first nucleated element classification process, the second nucleated element classification process, and the bacteria detecting process.

The urine sample analyzer 100 classifies the cells into a first group of large cells that include epithelial cells, atypical cells, and white blood cells and a second group of small cells that include sperms, trichomonas, and fungi by the fractionation process.

In the fractionation process S403, the particles in the first measurement specimen are first classified into the first group, the second group, and the bacteria group by using the FSCP and the FSCW. The appearing regions of nucleated formed elements in the characteristic parameter space specified by the FSCP and the FSCW will be described with reference to FIG. 11. When the particles in the first measurement specimen are plotted based on the FSCP and the FSCW, the nucleated formed elements of the first group and the second group are plotted in a region R11 illustrated in FIG. 11. The nucleated formed element group including bacteria is plotted in a region R12. The particles plotted in a region other than the regions R11 and R12 are detected as foreign substances and removed from analysis targets.

Figure 11:
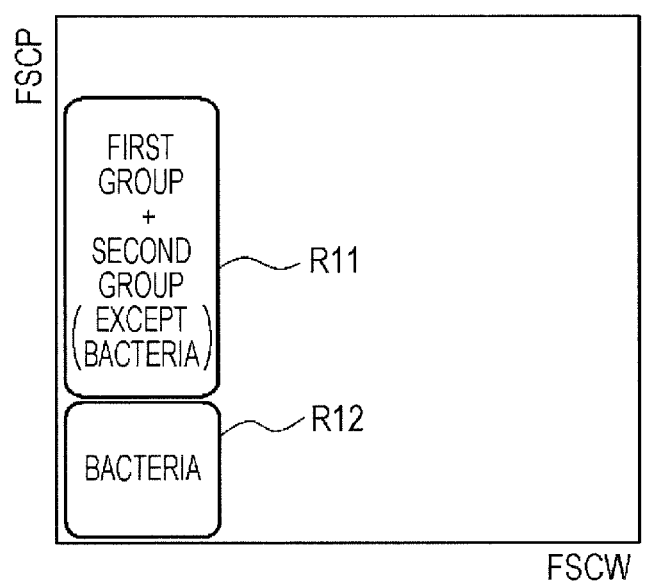
FIG. 11 is a view illustrating appearing regions of nucleated formed elements in a characteristic parameter space specified by a forward scattered light intensity and a forward scattered light pulse width.

Subsequently, the particle population plotted in the region R11 of FIG. 11 is classified into the first group and the second group by using the FSCP and the FLHP1. The particle group plotted in the region R11 of FIG. 11 is plotted in the characteristic parameter space specified by the FSCP and the FLHP1 illustrated in FIG. 12. The nucleated formed elements of the first group are plotted in the region R21 illustrated in FIG. 12. The nucleated formed elements of the second group are plotted in the region R22.

Figure 12:
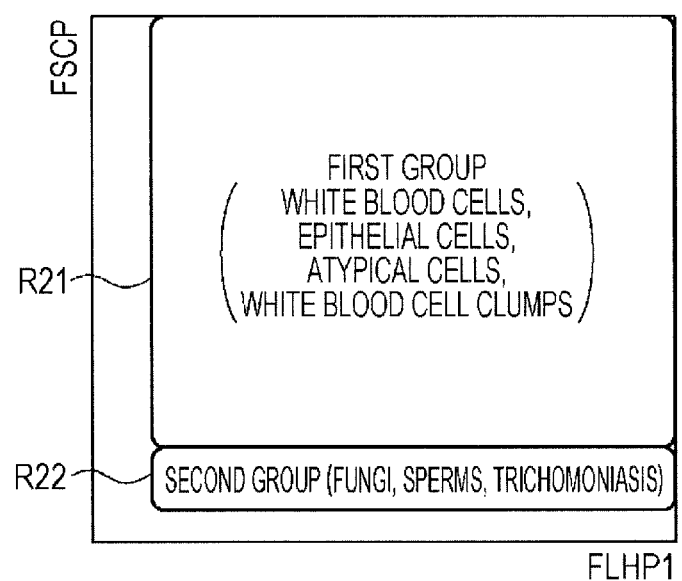
FIG. 12 is a view illustrating appearing regions of nucleated formed elements in a characteristic parameter space specified by a forward scattered light intensity and a first fluorescence intensity with high sensitivity.

In the first nucleated element classification process S404, the first group of particle populations plotted in the region R21 of FIG. 12 is classified into the third group of nucleated formed elements, white blood cells, and epithelial cells using the FSCW and the FLLA. The counted values of white blood cells and epithelial cells are obtained. The third group is a particle population that may contain atypical cells and white blood cell clumps.

Since the amount of nucleic acids in atypical cells, white blood cells, white blood cell clumps, and epithelial cells is larger than that in sperms, trichomonas, and fungi, the amount of fluorescence to be generated by light excitation is large. The fluorescence signal with low sensitivity is suitable for analysis. In the classification of the formed elements having a nuclear diameter larger than the diameter of the beam spot, the fluorescence light pulse area is appropriate as a parameter. The atypical cells, white blood cells, white blood cell clumps, and epithelial cells have a nuclear diameter larger than the diameter of the beam spot. Accordingly, in the first nucleated element classification process, the FLLA is used.

A characteristic parameter space specified by the FSCW and the FLLA (hereinafter referred to as "FSCW-FLLA space") will be described with reference to FIG. 13. The nucleated formed elements of the first group are plotted in the FSCW-FLLA space. As illustrated in the figure, white blood cells, epithelial cells, and the third group have different distribution regions of FLLA. This is because there is little difference in the amount of nucleic acids between white blood cells and epithelial cells, the amount of nucleic acids in atypical cells is larger than that in white blood cells or epithelial cells, and the FLLA reflects the amount of nucleic acids.

Figure 15A:
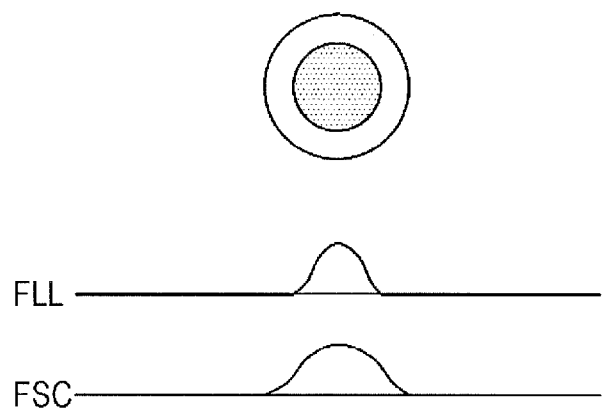
FIG. 15A is a pattern diagram to explain the waveform of the optical signal of atypical cells.
Figure 15B:
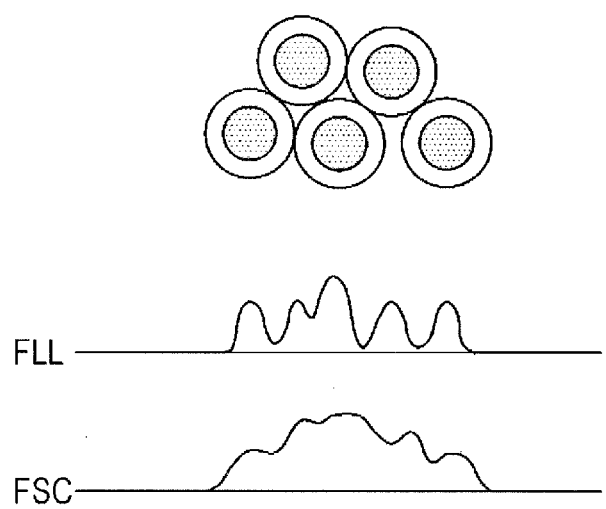
FIG. 15B is a pattern diagram to explain the waveform of the optical signal of white blood cell clumps.

As illustrated in FIG. 15B, as for white blood cell clumps, a plurality of white blood cells interacts with one another to form an aggregate. In the FLL, a plurality of nuclei of the white blood cells contained in the white blood cell clumps may be overlapped with one another to form a pulse. The FLLA of the white blood cell clumps is higher than that of white blood cells or epithelial cells. There is little difference in the FLLA between atypical cells and white blood cells.

Figure 13:
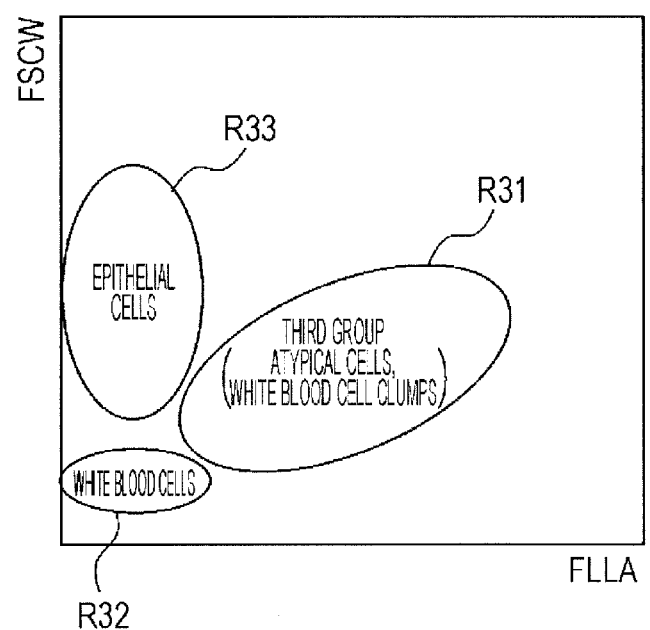
FIG. 13 is a view illustrating appearing regions of nucleated formed elements in a characteristic parameter space specified by a forward scattered light pulse width and a fluorescence pulse area with low sensitivity.

As illustrated in FIG. 13, white blood cells and epithelial cells have different distribution regions of FSCW. This is because the size of epithelial cells is larger than that of white blood cells, and the FSCW reflects the size of particles.

The atypical cells are cancerous cells such as transitional cell carcinoma cells or squamous cell carcinoma cells, and have a size larger than that of white blood cells. Since a plurality of white blood cells interacts with one another, the white blood cell clumps have a size larger than that of white blood cells and thus have the same size as that of atypical cells in many cases. When the atypical cells are contained in the urine sample, the atypical cells appear in the region R31 of the FSCW-FLLA space. When the white blood cell clumps are contained in the urine sample, the white blood cell clumps appear in the region R31 of the FSCW-FLLA space.

In the first nucleated element classification process S404, the particles plotted in the region R31 are detected as the third group, the particles plotted in the region R32 are counted as the white blood cells, and the particles plotted in the region R33 are counted as the epithelial cells.

Figure 14A:
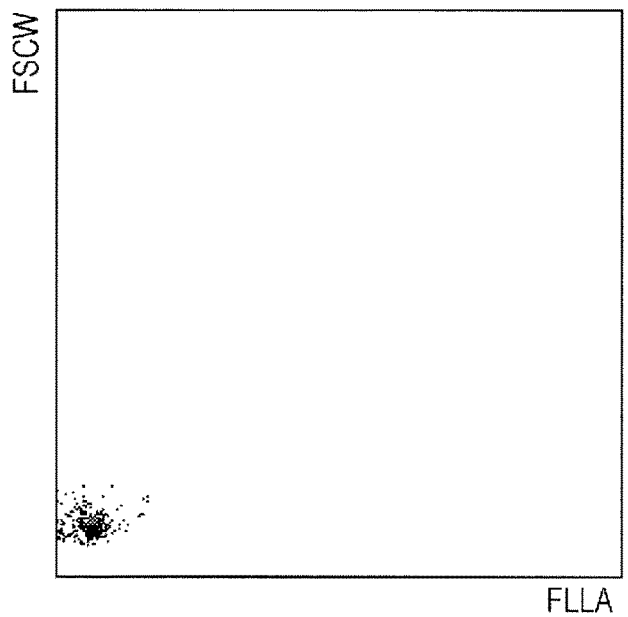
FIG. 14A is a scattergram illustrating an example of the detection result of white blood cells.
Figure 14B:
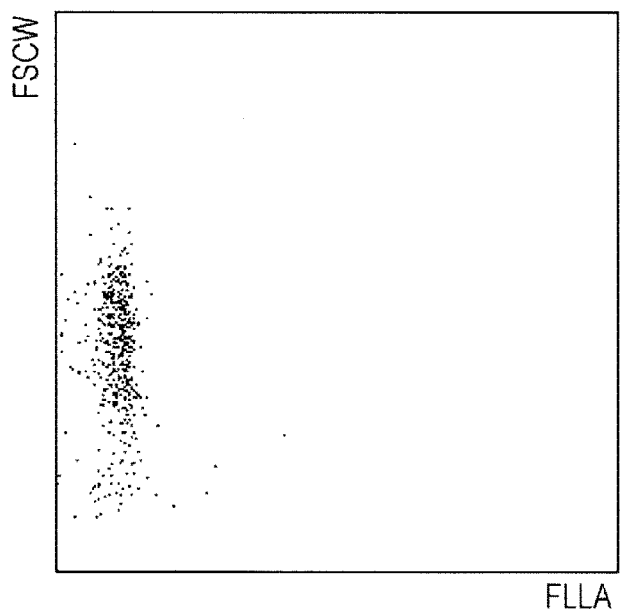
FIG. 14B is a scattergram illustrating an example of the detection result of epithelial cells.
Figure 14C:
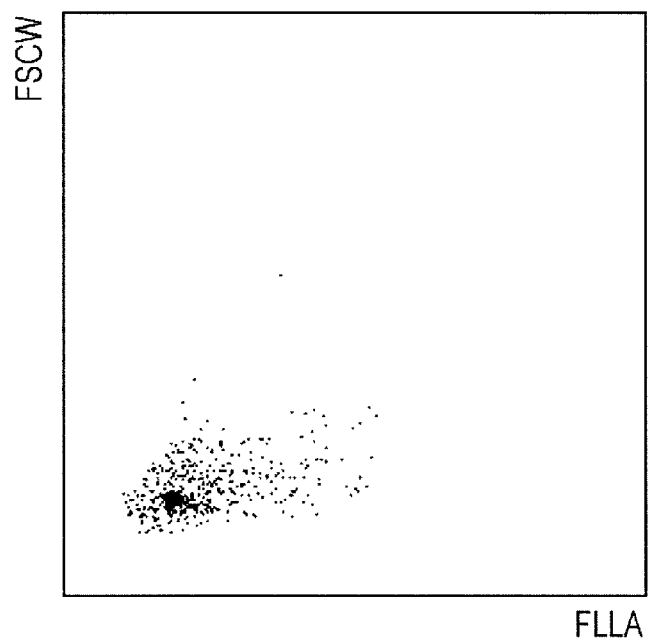
FIG. 14C is a scattergram illustrating an example of the detection result of a third group of particle populations.

FIGS. 14A to 14C illustrate the results of the nucleated elements actually detected in the first nucleated element classification process S404. FIG. 14A illustrates the result of measurement of the urine sample containing white blood cells, and particles appear at the position in the region R32. FIG. 14B illustrates the result of measurement of the urine sample containing epithelial cells, and particles appear at the position in the region R33. FIG. 14C illustrates the result of measurement of the urine sample containing atypical cells, and particles appear at the position in the region R31.

Thus, according to the sample analyzer 100 of the embodiment, the use of the FSCW that is the first parameter for reflecting a cell size and the FLLA that is the second characteristic parameter for reflecting the amount of nucleic acids in cells enables the white blood cells, epithelial cells, and atypical cells in urine to be classified.

In the atypical cell detecting process S405, the particle population plotted in the region R31 illustrated in FIG. 13 is classified into atypical cells and white blood cell clumps using the FSC-DS/P and the FL-DS/P, and the counted values thereof are determined.

In the atypical cells which are not in a mitotic phase and are not agglutinated, the pulse of FSC or FLL is monophasic in many cases as illustrated in FIG. 15A. On the other hand, in the white blood cell clumps, a plurality of white blood cells is agglutinated. Thus, the signal intensity intricately changes depending on the positional relationship between the white blood cells and the positional relationship between the nuclei. As illustrated in FIG. 15B, the pulse is multiphasic in many cases. Hence, the DS/P to reflect whether the pulse is monophasic or multiphasic reflects whether cells are independent or a plurality of the cells is linked. Therefore, the FSC-DS/P and the FL-DS/P are suitable as parameters for classifying atypical cells and white blood cell clumps.

Figure 16:
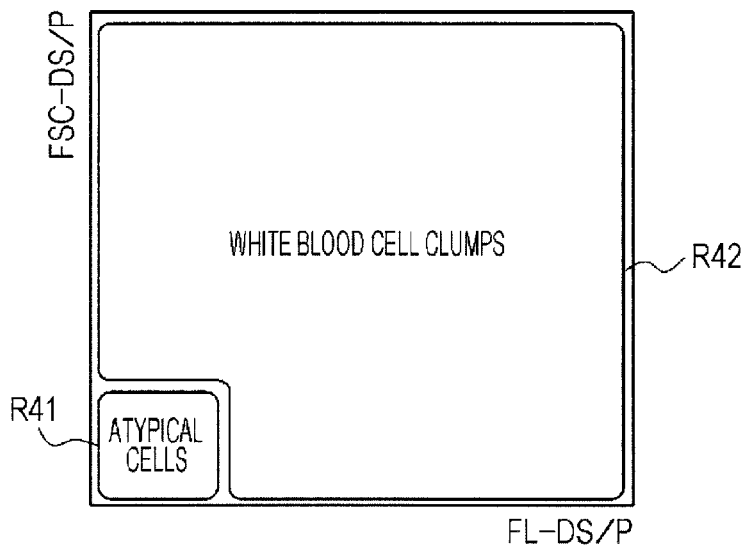
FIG. 16 is a view illustrating appearing regions of nucleated formed elements in the characteristic parameter space specified by the forward scattered light difference integrated value-peak level ratio and the fluorescent light difference integrated value-peak level ratio.

A characteristic parameter space specified by the FSC-DS/P and the FL-DS/P (hereinafter "two-dimensional DS/P space") will be described with reference to FIG. 16. The nucleated formed elements of the third group are plotted in the two-dimensional DS/P space. As illustrated in the figure, atypical cells and white blood cell clumps have different distribution regions in both the FSC-DS/P and the FL-DS/P.

Since the pulse of atypical cells is monophasic in many cases, the values of FSC-DS/P and FL-DS/P are relatively smaller than those of white blood cell clumps. Since the pulse of white blood cell clumps is multiphasic in many cases, the values of FSC-DS/P and FL-DS/P are relatively larger than those of atypical cells. When the atypical cells are contained in the urine sample, the atypical cells appear in the region R41 of the two-dimensional DS/P space. When the white blood cell clumps are contained in the urine sample, the white blood cell clumps appear in the region R42 of the two-dimensional DS/P space.

Figure 17:
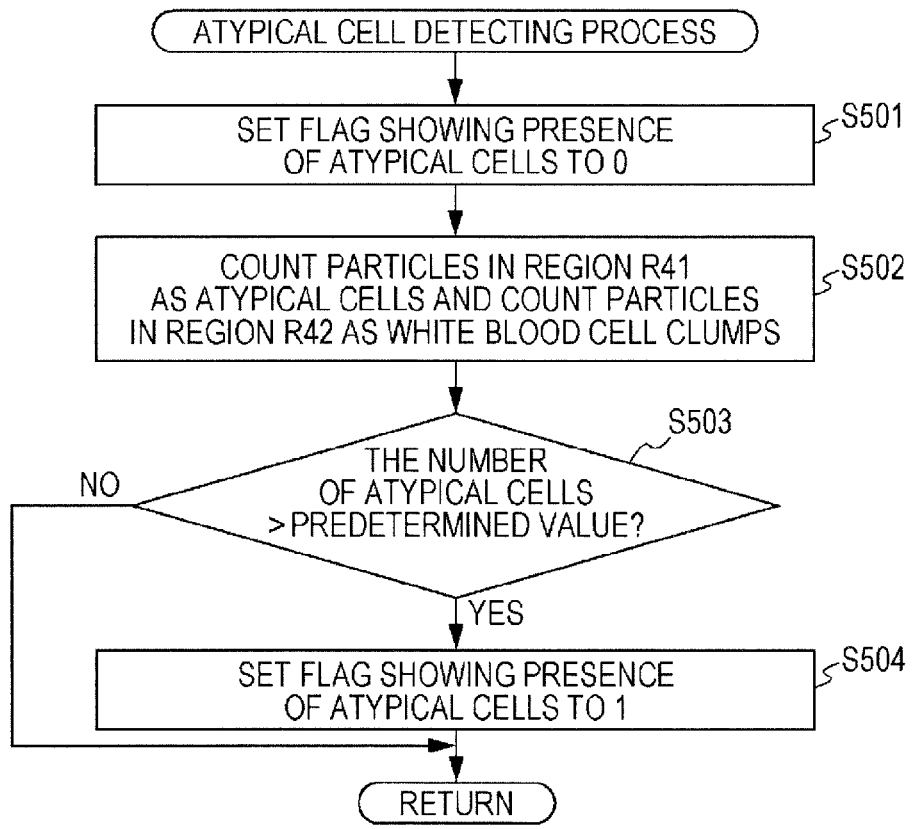
FIG. 17 is a flow chart illustrating a procedure of an atypical cell detecting process.

The atypical cell detecting process S405 will be further described with reference to FIG. 17. After the start of the atypical cell detecting process S405, the CPU 401 first sets the flag showing the presence of the atypical cells to an initial value of 0 in Step S501. Then, the CPU 401 counts the particles plotted in the region R41 as atypical cells and counts the particles plotted in the region R42 as white blood cell clumps using the FSC-DS/P and the FL-DS/P in Step S502. Subsequently, the CPU 401 determines whether the number of atypical cells is larger than a predetermined value in Step S503, and sets the flag showing the presence of the atypical cells to 1 when the number of atypical cells is larger than the predetermined value in Step S504, and terminates the atypical cell detecting process. When the number of atypical cells is the predetermined value or less in Step S503, the CPU 401 directly terminates the atypical cell detecting process.

Figure 18A:
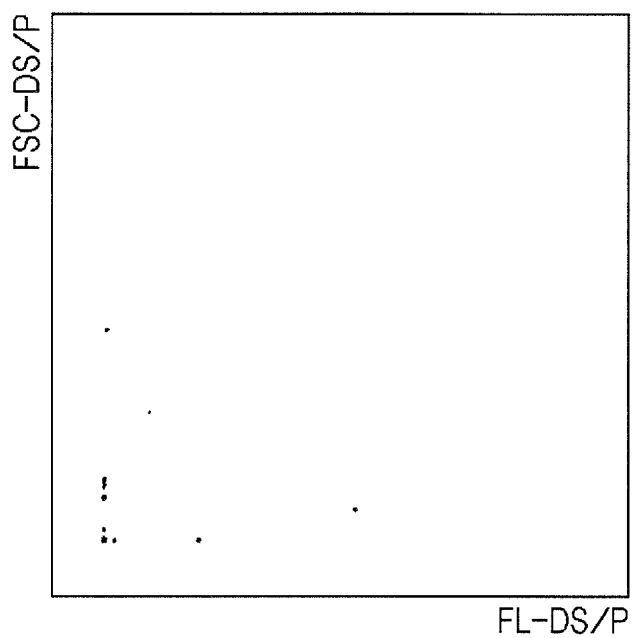
FIG. 18A is a scattergram illustrating an example of the detection result of atypical cells.
Figure 18B:
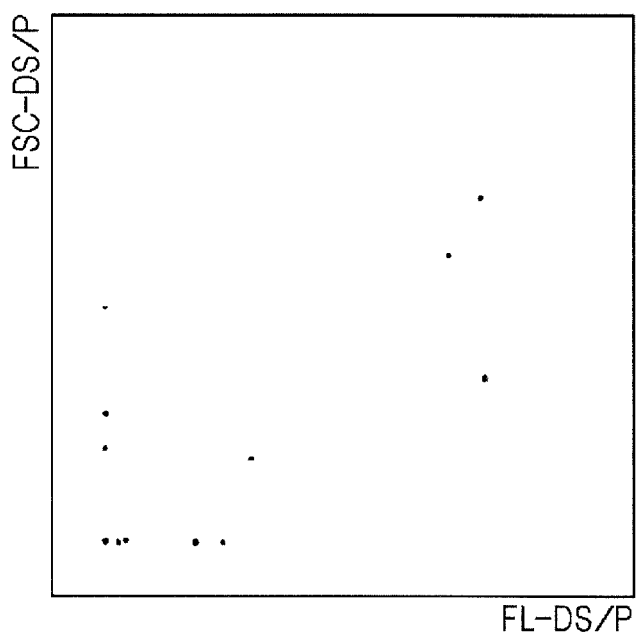
FIG. 18B is a scattergram illustrating an example of the detection result of white blood cell clumps.

FIGS. 18A to 18B illustrate the results of the nucleated elements actually detected in the atypical cell detecting process S405. FIG. 18A illustrates the result of measurement of the urine sample containing atypical cells, and particles appear at the position in the region R41. FIG. 18B illustrates the result of measurement of the urine sample containing white blood cell clumps, and particles appear at the position in the region R42.

In the second nucleated element classification process S406, the particle group plotted in the region R22 of FIG. 12 is classified into trichomonas, fungi, and sperms using the FSCP and the FLHP1, and the counted values thereof are determined.

Since the amount of nucleic acids in sperms, trichomonas, and fungi is smaller than that in white blood cells, white blood cell clumps, epithelial cells, and atypical cells, the amount of fluorescence to be generated by light excitation is relatively smaller, compared to the cells of the first group. Therefore, the fluorescence signal with high sensitivity is suitable for the analysis of sperms, trichomonas, and fungi. In the classification of the formed elements having a nuclear diameter smaller than the diameter of the beam spot, the fluorescence intensity is appropriate as a parameter. Sperms, trichomonas, and fungi have a nuclear diameter smaller than the diameter of the beam spot. Accordingly, in the second nucleated element classification process, the FLHP1 is used.

Figure 19:
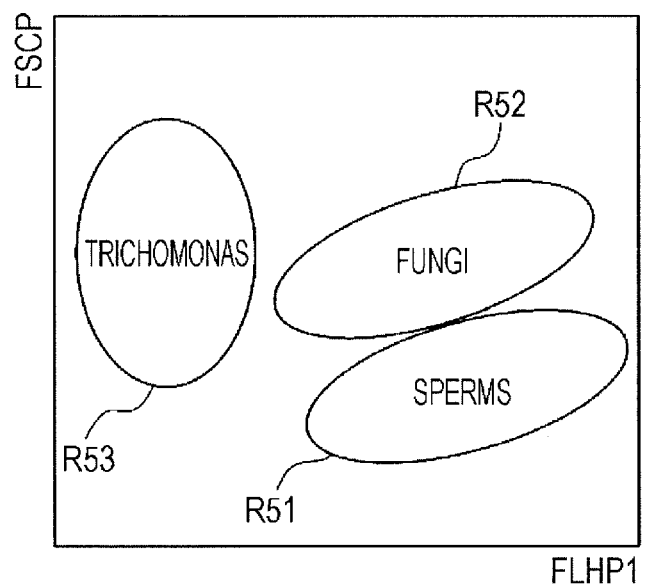
FIG. 19 is a view illustrating appearing regions of nucleated formed elements in a characteristic parameter space specified by a forward scattered light intensity and a first fluorescence intensity with high sensitivity.

FIG. 19 illustrates a characteristic parameter space specified by the FSCP and the FLHP1 (hereinafter referred to as "FSCP-FLHP1 space"). The nucleated formed elements of the second group are plotted in the FSCP-FLHP1 space. The sperms, fungi, and trichomonas differ in the distribution region in the FSCP-FLHP1 space. This is because the sperms, fungi, and trichomonas differ in terms of the amount of nucleic acids and the size. The particles plotted in the region R51 are counted as sperms. The particles plotted in the region R52 are counted as fungi. The particles plotted in the region R53 are counted as trichomonas.

Figure 20A:
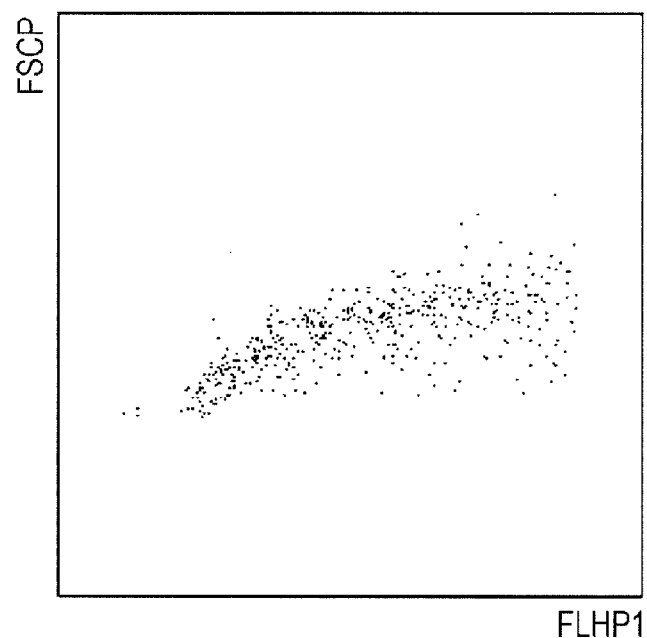
FIG. 20A is a scattergram illustrating an example of the detection result of fungi.
Figure 20B:
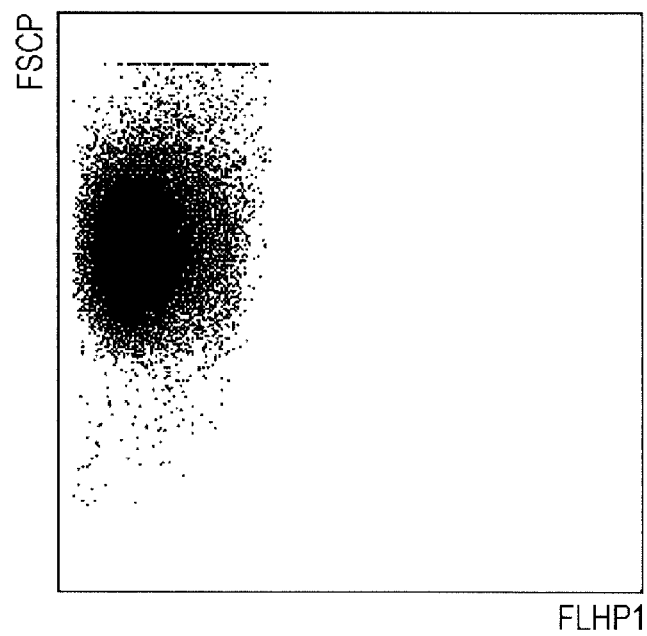
FIG. 20B is a scattergram illustrating an example of the detection result of trichomonas.
Figure 20C:
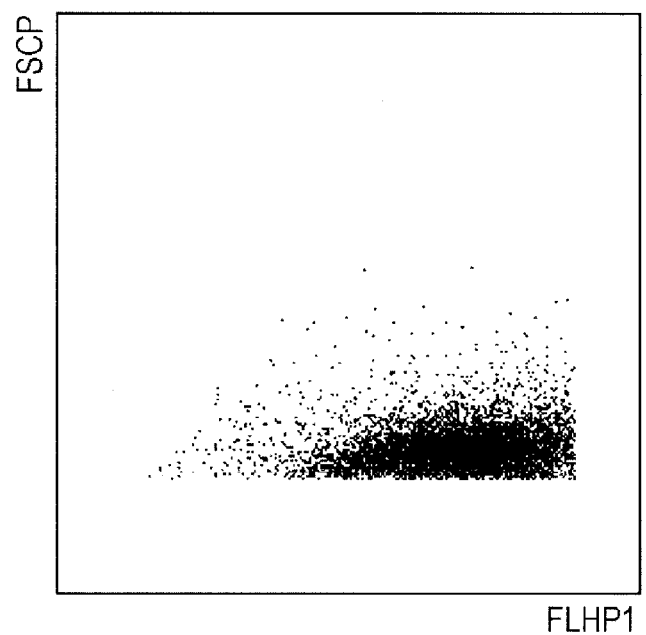
FIG. 20C is a scattergram illustrating an example of the detection result of sperms.

FIGS. 20A to 20C illustrate the results of the nucleated elements actually detected in the second nucleated element classification process S406. FIG. 20A illustrates the result of measurement of the urine sample containing fungi, and particles appear at the position of the region R52. FIG. 20B illustrates the result of measurement of the urine sample containing trichomonas, and particles appear at the position of the region R53. FIG. 20C illustrates the result of measurement of the urine sample containing sperms, and particles appear at the position of the region R51.

In the bacteria detecting process S407, bacteria of the particle population plotted in the region R12 of FIG. 11 are counted using the FSCP and the FLHP2.

The bacteria have a very small size compared to other nucleated cells such as white blood cells and also have a small amount of nucleic acids. Thus, the amount of fluorescence is smaller, compared to other nucleated cells. The bacteria are microscopic, and have a particle diameter smaller than the diameter of the beam spot. Therefore, the bacteria are detected using the FLHP2 that is the intensity of the fluorescence signal with highest sensitivity.

Figure 21:
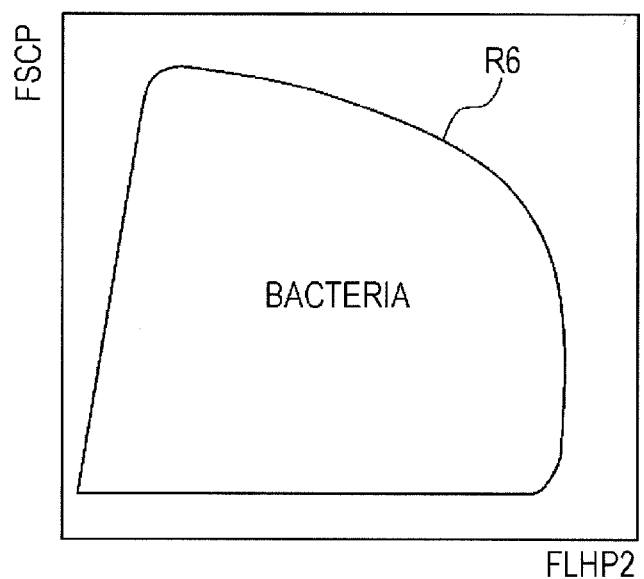
FIG. 21 is a view illustrating appearing regions of bacteria in a characteristic parameter space specified by a forward scattered light intensity and a second fluorescence intensity with high sensitivity.

FIG. 21 illustrates a characteristic parameter space specified by the FSCP and the FLHP2 (hereinafter referred to as "FSCP-FLHP2 space"). The particle population plotted in the region R12 of FIG. 11 is expanded in the FSCP-FLHP2 space. In the FSCP-FLHP2 space illustrated in FIG. 21, bacteria appear in the region R6. Nucleated cells other than bacteria may be plotted in the FSCP-FLHP2 space illustrated in FIG. 21. Almost all the nucleated cells other than bacteria are saturated and excluded from analysis targets when converted into fluorescence signals with high sensitivity. In the region having a fluorescence intensity lower than that of the region R6, foreign substances having no nucleic acids appear. The particles plotted in the region R6 are counted as bacteria.

Figure 22:
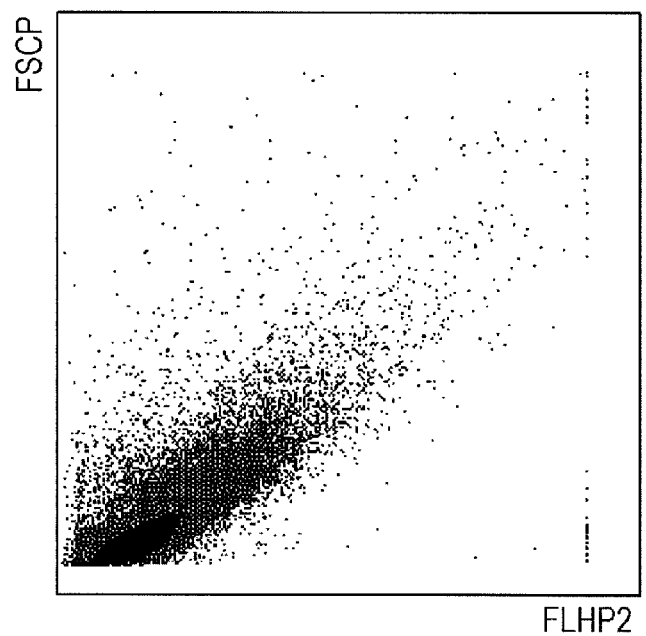
FIG. 22 is a scattergram illustrating an example of the detection result of bacteria.

FIG. 22 illustrates the result of bacteria actually detected in the bacteria detecting process S407. FIG. 22 illustrates the result of measurement of the urine sample containing bacteria.

Refer to FIG. 10 again. After the measurement data analysis process is finished, the CPU 401 returns the process to the main routine.

Refer to FIG. 7 again. The CPU 401 displays the analysis result obtained by the measurement data analysis process on the display unit 409 in Step S110, and terminates the process. The analysis result includes the calculated result of the detected formed elements and reference information as a reference for diagnosis. When the flag showing the presence of atypical cells is set to 1, information for indicating the presence of atypical cells is output as the reference information.

Figure 23:
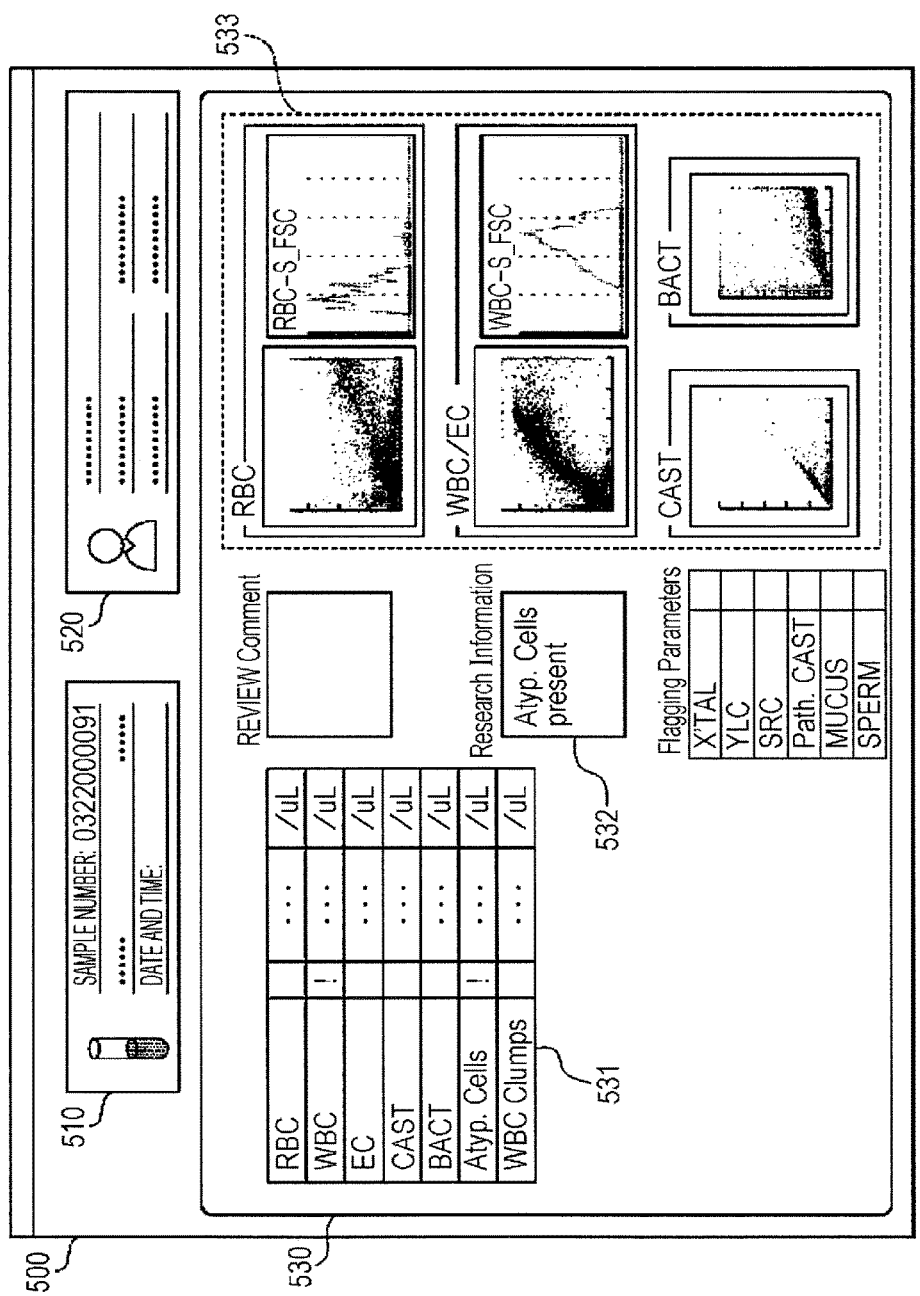
FIG. 23 is a view illustrating an analysis result screen.

The analysis result to be displayed will be further described with reference to FIG. 23. An analysis result screen 500 is displayed on the display unit 409. The analysis result screen 500 includes a sample information display region 510, a patient information display region 520, and a measurement result display region 530. The measurement result display region 530 includes a measurement value display region 531, a reference information display region 532, and an image display region 533.

The information on urine samples originally derived from the analysis result displayed on the analysis result screen 500 is displayed in the sample information display region 510. The information on patients whose urine samples are collected is displayed in the patient information display region 520.

Counted values of items obtained by the measurement data analysis process are displayed in the measurement value display region 531. The numerical information to be displayed includes counted values of red blood cells (RBC), white blood cells (WBC), epithelial cells (EC), casts (CAST), bacteria (BACT), atypical cells (Atyp.Cells), and white blood cell clumps (WBC Clumps).

Reference information for users is displayed in the reference information display region 532 when the measurement result to be reported to users (such as abnormalities of urine samples) is obtained by the measurement data analysis process. When the flag showing the presence of atypical cells is set to 1 in the measurement data analysis process, the information for indicating the presence of atypical cells "Atyp.Cells present" is displayed in the reference information display region 532. Accordingly, the information for indicating the presence of atypical cells, which is clinically useful information, can be provided to users.

The scattergrams and histograms of measurement results are displayed in the image display region 533.

OTHER EMBODIMENTS

In the embodiment described above, the configuration of classifying cells by plotting particles in the characteristic parameter spaces of FIGS. 11, 12, 13, and 16 in this order has been described. However, it is not limited to this embodiment. In other words, it is not necessary to repeat the process of extracting particles plotted in a predetermined area of a characteristic parameter space and plotting the extracted particles in the next characteristic parameter space.

For example, the conditions for identifying a particle as a certain type of cell are defined by "having a parameter within the range specified in the first characteristic parameter space and having a parameter within the range specified in the second characteristic parameter space". Such conditions are defined for each type of cell. The particle satisfying one of the conditions is identified as a cell type corresponding to the condition. Specifically, nucleated formed elements having the FSCP and the FLHP1 in the region R21 of FIG. 12 and having the FSCW and the FLLA in the region R32 of FIG. 13 are detected as white blood cells. Nucleated formed elements having the FSCP and the FLHP1 in the region R21 of FIG. 12, having the FSCW and the FLLA in the region R31 of FIG. 13, and having the FSC-DS/P and the FL-DS/P in the region R41 of FIG. 16 are detected as atypical cells. Other types of cells can be subjected to cell-type identification in the same manner as described.

In the embodiment described above, the two-dimensional characteristic parameter space has been illustrated, and the particles may be plotted in a three- or high-dimensional characteristic parameter space.

Figure 24:
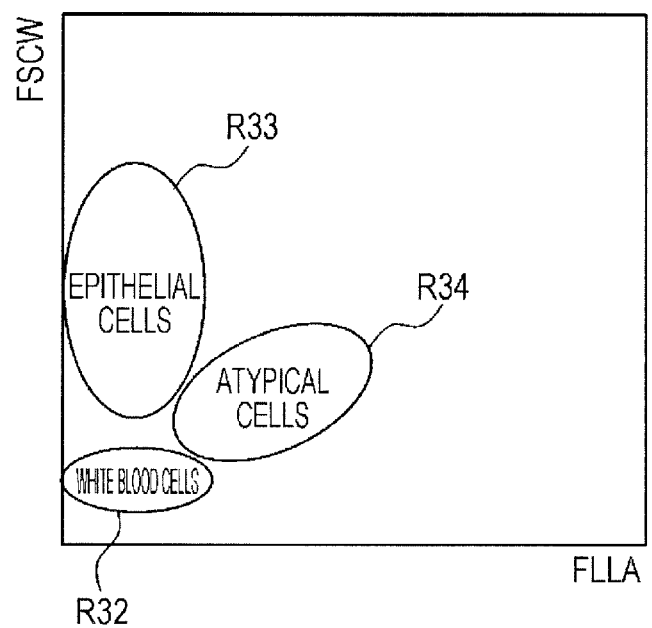
FIG. 24 is a view illustrating another example of appearing regions of nucleated formed elements in a characteristic parameter space specified by a forward scattered light pulse width and a fluorescence pulse area with low sensitivity.

In the embodiment described above, the nucleated formed elements of the third group classified in the first nucleated element classification process (FIG. 10) are further classified into white blood cell clumps and atypical cells. This is just a preferable example. As illustrated in FIG. 24, the region R32 of distribution of white blood cells, the region R33 of distribution of epithelial cells, and the region R34 of distribution of atypical cells are specified in the FSCW-FLLA space, and then the particles plotted in the region R34 may be detected as atypical cells using the FSCW and the FLLA.

In the embodiment described above, the counted values of the atypical cells are output. However, the counted values may not be output. Depending on the calculated result of atypical cells, only the information for indicating the presence of atypical cells may be output as the qualitative measurement result. When the number of white blood cell clumps detected is larger than a predetermined number, the counted values of the white blood cell clumps as well as information for indicating the presence of white blood cell clumps may be output. Depending on the calculated result of the white blood cell clumps without outputting the counted values of the white blood cell clumps, the information for indicating the presence of white blood cell clumps may be output as the qualitative measurement result.

In the embodiment described above, the atypical cells are distinguished from the white blood cell clumps using both the FSC-DS/P and the FL-DS/P, and only one of them may be used.

In the embodiment described above, the FSC-DS/P and the FL-DS/P are used as the characteristic parameter for distinguishing the atypical cells from the white blood cell clumps. In place of the FSC-DS/P and the FL-DS/P, other characteristic parameters to reflect whether the pulse is monophasic or multiphasic may be used. For example, the area of recess, the width of recess, the number of peaks in the pulse of forward scattered light signal or fluorescence signal can be alternatively used.

In the embodiment described above, the white blood cells, the epithelial cells, and the third group of particle populations are classified using the FSCW. In place of the FSCW, the SSCW, the FSCP, the SSCP, the FSCA or the SSCA may be used.

In the embodiment described above, the white blood cells, the epithelial cells, and the third group of particle populations are classified using the FLLA. The FLLW may be used in place of the FLLA.

In the embodiment described above, the form of detecting the atypical cells in urine by the urine sample analyzer has been described. However, it is not limited to this embodiment. In the urine sample analyzer, the atypical cells in the body fluid may be distinguished from other cells such as white blood cells and epithelial cells. The body fluid is a liquid filling the body or circulating in the body, except for blood and urine. Examples of the body fluid include cerebrospinal fluid (CSF: fluid filling the ventricle or subarachnoid cavity), fluid of the thoracic cavity (pleural fluid, PE: fluid collected in the pleural cavity), peritoneal fluid (fluid collected in the peritoneal cavity), cardiac sac fluid (fluid collected in the cardiac sac), and synovial fluid (synovial fluid: fluid present in joints, synovial bursa, peritenon). Other examples of the body fluid include dialysis fluid for peritoneal dialysis (CAPD) and intraperitoneal rinse. In this case, the urine sample analyzer can be configured to be selectively operable in a urine analysis mode for analyzing urine or a body fluid analysis mode for analyzing body fluid.

In the embodiment described above, the configuration of executing the measurement specimen preparing process, the anucleate element measuring process, the nucleated element measuring process, and the measurement data analysis process in this order has been described. It is also possible to execute the above processes in another order. For example, the configuration can be such that the second measurement specimen is prepared, the anucleate element measuring process is executed, the first anucleate element classification process and the second anucleate element classification process are executed, the first measurement specimen is prepared, the nucleated element measuring process is executed, and the first nucleated element classification process, the atypical cell detecting process, the second nucleated element classification process, and the bacteria detecting process are executed.

In place of the information processing unit 13 which has analyzed measurement data in the embodiment described above, the microcomputer 11 of the measuring unit 10 may analyze the measurement data.

What is claimed is:

1. A method for analyzing atypical cells in urine, comprising:
   (a) mixing urine, a diluent containing a surfactant, and a nucleic acid staining reagent to prepare a measurement specimen;
   (b) irradiating the measurement specimen with light to detect scattered light and to detect fluorescence light, with first sensitivity and second sensitivity higher than the first sensitivity, emitted from cells whose nucleic acids are stained; and
   (c) detecting atypical cells contained in the measurement specimen distinguishably from white blood cells based on the detected scattered light and the fluorescence light detected with the first sensitivity, and detecting bacteria contained in the measurement specimen based on the detected scattered light and the fluorescence light detected with the second sensitivity.

2. The method according to claim 1, wherein
in the step (c), the detected atypical cells are counted, and the method further comprises a step of outputting information indicating a presence of the atypical cells when a number of the atypical cells is larger than a predetermined number.

3. The method according to claim 1, wherein
in the step (c), the detected white blood cells and the atypical cells are counted, and
the method further comprises a step of displaying information based on a number of the atypical cells with a counting result of the white blood cells.

4. The method according to claim 1, wherein
in the step (c), the atypical cells contained in the measurement specimen are detected distinguishably from the white blood cells and epithelial cells based on the detected scattered light and the fluorescence light detected by the first sensitivity.

5. The method according to claim 1, wherein
in the step (c), the atypical cells contained in the measurement specimen are detected distinguishably from bacteria or fungi based on the detected scattered light and the fluorescence light detected by the first sensitivity.

6. The method according to claim 1, wherein
the atypical cells contained in the measurement specimen are distinguishably detected from the white blood cells based on a first characteristic parameter of the scattered light, the first parameter reflecting a cell size, and
a second characteristic parameter of the fluorescence light, the second parameter reflecting an amount of nucleic acids in cells.

7. The method according to claim 6, wherein
in the step (c), at least a part of nucleated cell population contained in the measurement specimen is classified, based on the first characteristic parameter and the second characteristic parameter, into a first cell population having the first and the second characteristic parameters in a predetermined range, a second cell population having the first characteristic parameter higher than the first characteristic parameter of the first cell population, a third cell population having the first characteristic parameter higher than the first characteristic parameter of the first cell population and the second characteristic parameter higher than the second characteristic parameter of the second population, and
the first to third cell populations are detected as white blood cells, epithelial cells, and atypical cells, respectively.

8. The method according to claim 1, further comprising a step of dividing the urine into at least a first aliquot and a second aliquot, wherein
in the step (a),
the first aliquot, the diluent, and the nucleic acid staining reagent are mixed to prepare a first measurement specimen as the measurement specimen,
the second aliquot, a second diluent different from the diluent, and a reagent different from the nucleic acid staining reagent are mixed to prepare a second measurement specimen,
in the step (c), white blood cells and atypical cells contained in the first measurement specimen are detected, and
the method further comprises a step of detecting red blood cells contained in the second measurement specimen.

9. The method according to claim 1, wherein
in the step (c), the atypical cells contained in the measurement specimen are detected distinguishably from the white blood cells and white blood cell clumps based on a third characteristic parameter based on the scattered light or the fluorescence light, in addition to the first characteristic parameter and the second characteristic parameter.

10. The method according to claim 9, wherein
in the step (c), the white blood cell clumps contained in the measurement specimen are detected distinguishably from the atypical cells and counted, and
the method further comprises a step of outputting information based on the number of the white blood cell clumps.

11. The method according to claim 9, wherein
the third characteristic parameter is a parameter indicating whether a pulse included in a signal that indicates a temporal change of an intensity of the scattered light or the fluorescence light is monophasic or multiphasic.

12. The method according to claim 11, wherein
the third characteristic parameter is a ratio between a difference integrated value and a peak value of the pulse.

13. The method according to claim 6, wherein
the first characteristic parameter is a peak value of a pulse included in the detected scattered light signal that indicates a temporal change of an intensity of the scattered light, a width of the pulse, or an area of the pulse.

14. The method according to claim 6, wherein
the second characteristic parameter is a width of a pulse included in the detected fluorescence signal that indicates a temporal change of an intensity of the fluorescence light, or an area of the pulse.

* * * * *